US009049990B2

(12) United States Patent
Sakashita

(10) Patent No.: US 9,049,990 B2
(45) Date of Patent: Jun. 9, 2015

(54) CORNEAL ENDOTHELIAL CELL PHOTOGRAPHING APPARATUS

(71) Applicant: NIDEK CO., LTD., Gamagori-shi, Aichi (JP)

(72) Inventor: Yusuke Sakashita, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 13/940,431

(22) Filed: Jul. 12, 2013

(65) Prior Publication Data

US 2014/0016094 A1    Jan. 16, 2014

(30) Foreign Application Priority Data

Jul. 12, 2012 (JP) ................................. 2012-156474

(51) Int. Cl.
*A61B 3/14* (2006.01)
*A61B 3/00* (2006.01)

(52) U.S. Cl.
CPC ................. *A61B 3/0058* (2013.01); *A61B 3/14* (2013.01)

(58) Field of Classification Search
CPC ........ A61B 3/152; A61B 3/145; A61B 3/103; A61B 3/113; A61B 3/14; A61B 3/1225; A61B 3/024; A61B 3/1015
USPC ......... 351/208, 200, 209–210, 205–206, 211, 351/221–222, 246
See application file for complete search history.

(56) References Cited

U.S. PATENT DOCUMENTS

2002/0080329 A1* 6/2002 Kasahara ...................... 351/200
2012/0249957 A1* 10/2012 Shibata et al. ................ 351/206
2012/0249958 A1* 10/2012 Honda et al. .................. 351/206

FOREIGN PATENT DOCUMENTS

JP           06-327635         11/1994
JP           11-070079          3/1999
JP        2011-245184 A        12/2011

* cited by examiner

*Primary Examiner* — Dawayne A Pinkney
(74) *Attorney, Agent, or Firm* — Rankin, Hill & Clark LLP

(57) ABSTRACT

A corneal endothelial cell photographing apparatus for photographing an endothelial cell in the cornea of the examinee's eye includes an optical system, an image processor, and a display controller. The optical system includes an illuminating optical system for irradiating the cornea with illuminating light, and a light receiving optical system including a light detector and configured to receive reflected light from the cornea including the endothelial cell. The image processor analyzes each of endothelial cell images photographed at different positions on the cornea, and acquires an integrated analysis result by integrating the result of analysis of each of the endothelial cell images. The display controller displays the endothelial cell images simultaneously on a monitor with reference to an endothelial cell image photographed at a central portion of the cornea, and displays the integrated analysis result on the same screen as for the endothelial cell images.

18 Claims, 16 Drawing Sheets

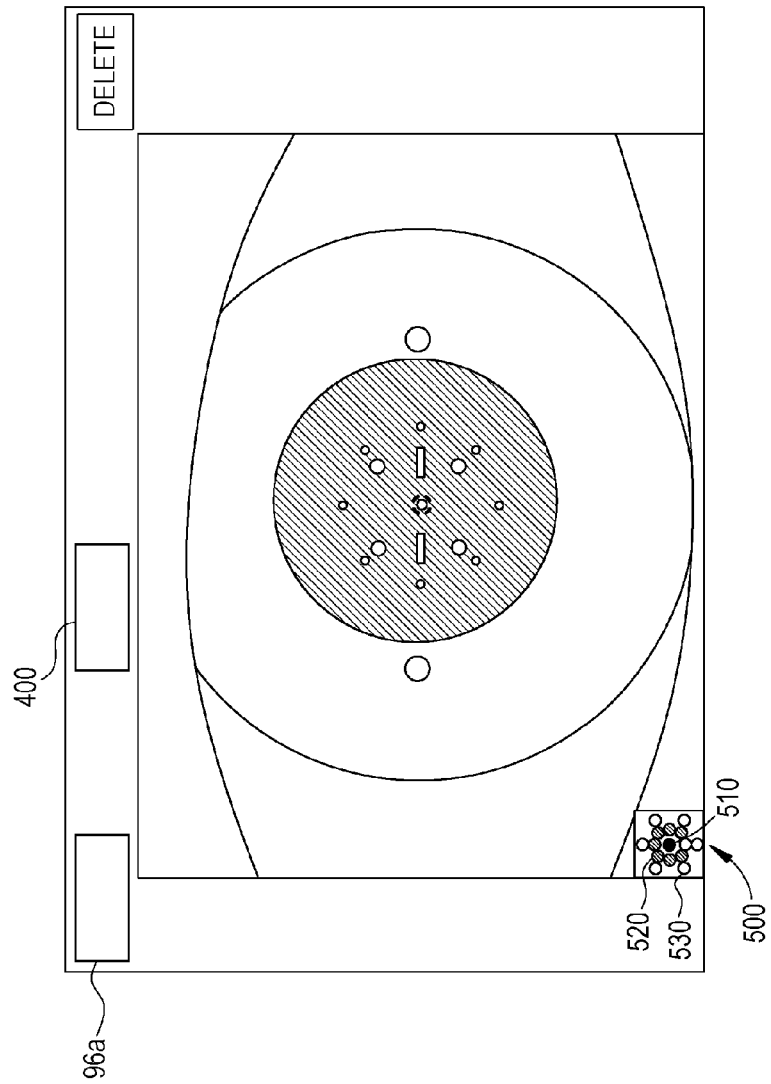

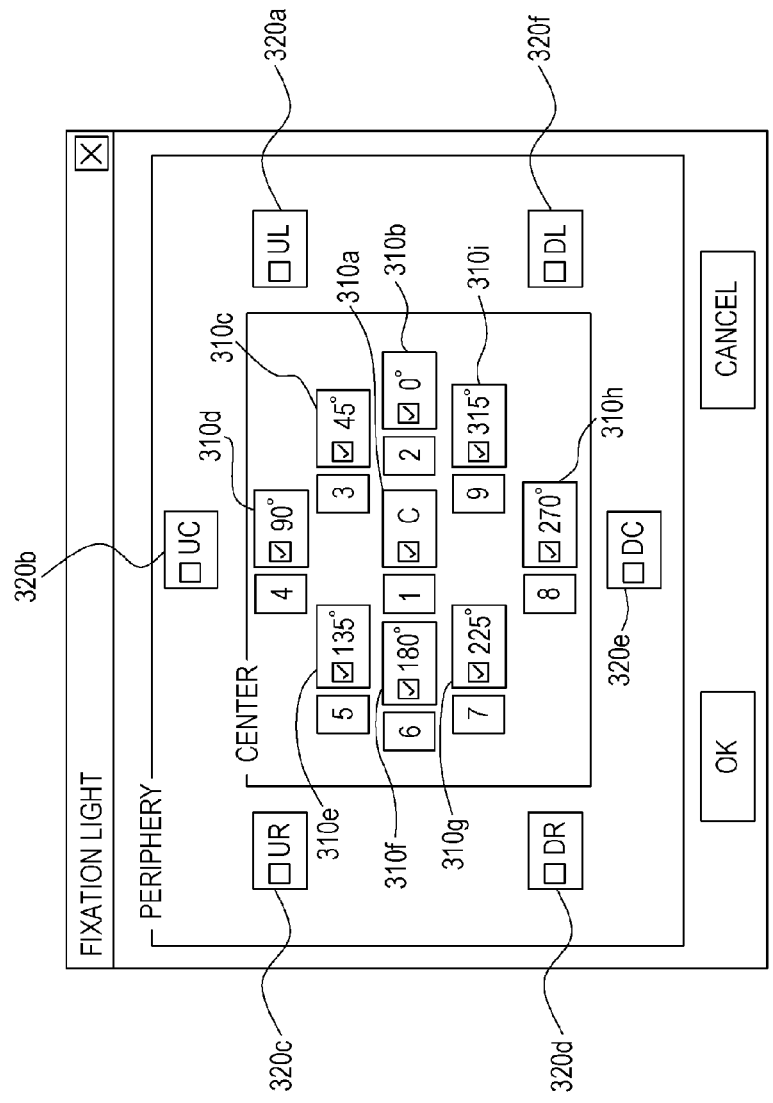

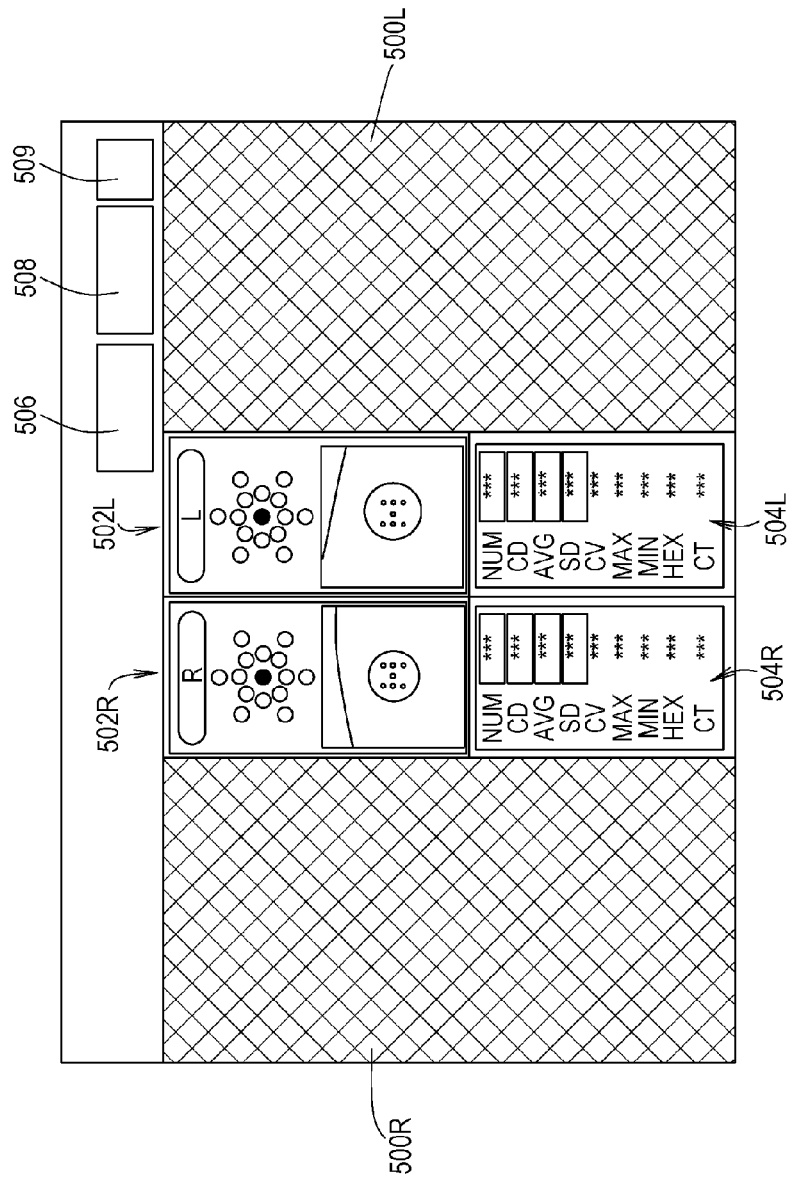

US 9,049,990 B2

CORNEAL ENDOTHELIAL CELL PHOTOGRAPHING APPARATUS

CROSS-REFERENCE TO RELATED APPLICATION

This application is based on Japanese Patent Application No. 2012-156474 filed with the Japan Patent Office on Jul. 12, 2012, the entire content of which is hereby incorporated by reference.

BACKGROUND

1. Technical Field

The present disclosure relates to a corneal endothelial cell photographing apparatus.

2. Related Art

A corneal endothelial cell photographing apparatus for photographing an endothelial cell image of the eye of an examinee (hereinafter also referred to as "examinee's eye") is known (see, for example, JP-A-2011-245184). The apparatus irradiates the cornea of the examinee's eye with illuminating light, and receives reflected light from the endothelial cells in the cornea, thus photographing an endothelial cell image.

The apparatus analyzes the obtained endothelial cell image and outputs an analysis result including the number of endothelial cells and their density, for example. However, the conventional apparatus displays only a single endothelial cell image and the analysis result for the endothelial cell image on a monitor.

The conventional apparatus includes a central sight fixation light corresponding to the central portion of the cornea and a plurality of peripheral sight fixation lights disposed on a circumference with respect to the central sight fixation light, and is configured so that the photographing position can be changed. The peripheral sight fixation lights are disposed such that the angle of sight of the examinee's eye can be swung in a range of 25° to 30°. An endothelial cell image at a position approximately 7 mm away from the corneal central portion is obtained.

SUMMARY

A corneal endothelial cell photographing apparatus for photographing an endothelial cell in the cornea of the examinee's eye, includes an optical system, an image processor, and a display controller, wherein the optical system includes an illuminating optical system for irradiating the cornea with illuminating light, and a light receiving optical system including a light detector and configured to receive reflected light from the cornea including the endothelial cell, the image processor analyzes each of a plurality of endothelial cell images photographed at different positions on the cornea, and acquires an integrated analysis result by integrating the result of analysis of each of the plurality of endothelial cell images, and the display controller displays the plurality of endothelial cell images simultaneously on a monitor with reference to an endothelial cell image photographed at a central portion of the cornea, and displays the integrated analysis result on the same screen as for the plurality of endothelial cell images.

BRIEF DESCRIPTION OF DRAWINGS

FIG. 4A illustrates a display example with an alignment deviation, and FIG. 4B illustrates a display example with appropriate alignment;

FIG. 9 is a diagram illustrating an exemplary photographing screen on the monitor;

FIG. 10 is a diagram illustrating an exemplary fixation position setting screen on the monitor;

FIG. 13A is a diagram illustrating an example of a photographing result screen (single display) according to the present embodiment;

DETAILED DESCRIPTION

Figure 1:
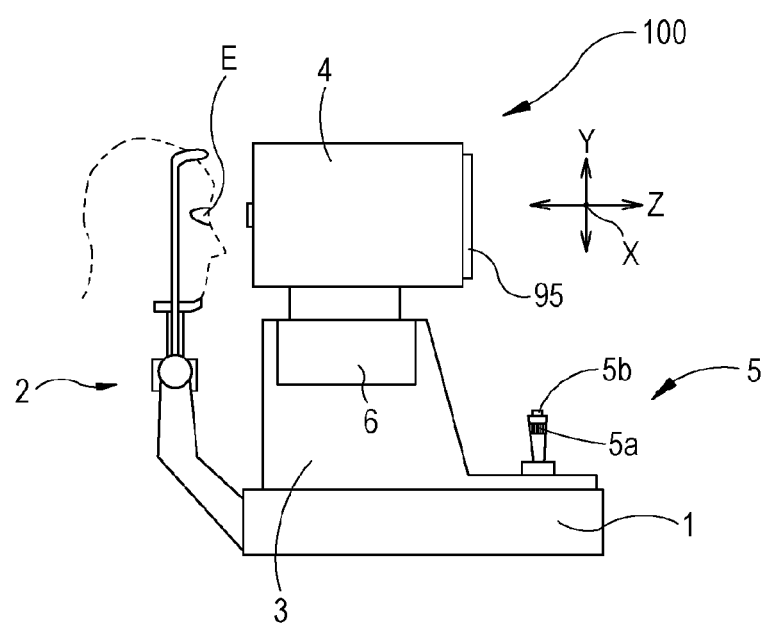
FIG. 1 is a side view schematically illustrating a configuration of a corneal endothelial cell photographing apparatus according to an embodiment of the disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the case of measurement of an eye whose corneal endothelium is difficult to observe, such as a diseased eye, the number of cells shown in an image may be very small. For automatic analysis, the number of cells of the corneal endothelium is preferably not less than 100 at the minimum. However, in the case of a diseased eye, it is normally found that the number of detected cells is 50 or less. In the conventional apparatus, the swing angle of the peripheral sight fixation lights with respect to the central sight fixation light is large. Thus, for the evaluation of the number of cells near the center, an endothelial cell image obtained by using the central sight fixation light has been used. As a result, the reliability of the analysis result may be lowered.

An object of an embodiment of the present disclosure is to provide a corneal endothelial cell photographing apparatus that can output a highly reliable processing result.

A corneal endothelial cell photographing apparatus includes: a main unit that includes an illumination optical system, an imaging optical system, and a fixation optical system; a setting unit configured to preliminarily set illumination positions and an illumination order of the plurality of fixation lamps; a controller configured to obtain an endothelial image at a first fixation position, control the fixation optical system corresponding to a determination result for propriety of the endothelial image obtained at the first fixation position to light a fixation lamp corresponding to a second fixation position preliminarily set by the setting unit, and control the illumination optical system and the imaging optical system to obtain an endothelial image at the second fixation position; a monitor configured to display the endothelial image; and an operating unit configured to input a signal for operating at least the controller.

The present photographing apparatus can output a highly reliable processing result.

An exemplary corneal endothelial cell photographing apparatus (hereinafter also referred to simply as an apparatus) according to one embodiment of this disclosure will be described with reference to the accompanying drawings. FIGS. 1 to 12 simply illustrate one example of this apparatus, and do not limit the configuration of the apparatus of this embodiment.

Hereinafter, an outline of this embodiment will be described. In the following description, any positional descriptive terms refer to the organism in its standard anatomical position. As illustrated in FIG. 1, a right and left direction of an examinee's eye to be observed is defined as an X-direction, an up and down direction is defined as a Y-direction, and a back and forth direction is defined as a Z-direction.
<Outline>

As illustrated in FIG. 1, an apparatus 100 according to this embodiment takes an image of a corneal portion of an examinee's eye E. This apparatus 100 is what is called a stationary apparatus. This apparatus 100 includes a base 1, a head support unit 2 mounted on the base 1, a movable table 3 movably disposed on the base 1, and a photographing unit (main unit) 4 movably disposed with respect to the movable table 3. The photographing unit 4 includes a monitor 95. The movable table 3 can move in the X- and Z-directions on the base 1 by operation of a joystick 5.

Figure 2:
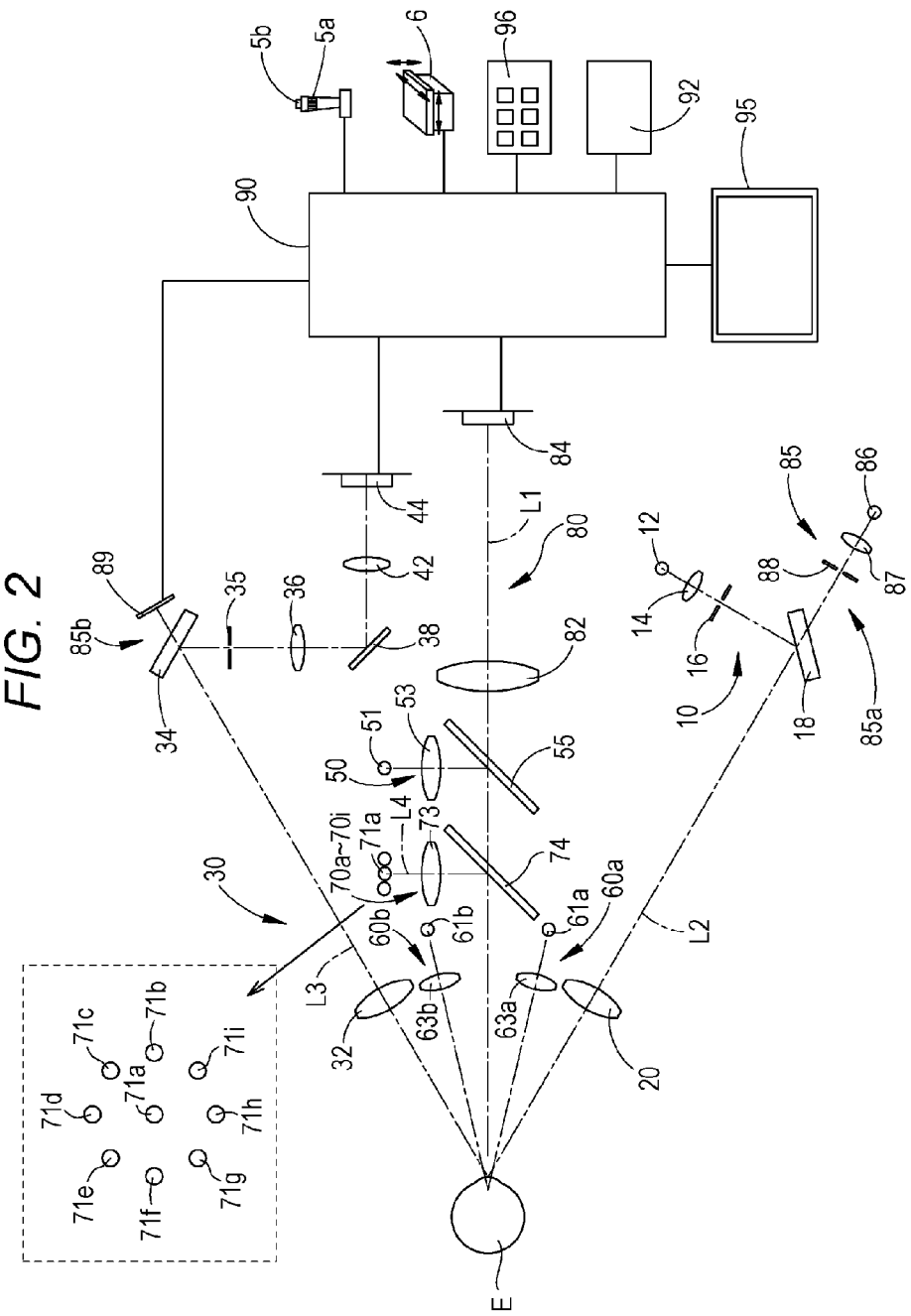
FIG. 2 is a schematic diagram illustrating exemplary schematic configurations of an optical system and a control system in the corneal endothelial cell photographing apparatus.

As illustrated in FIG. 2, the photographing unit 4 of this apparatus 100 includes optical systems for imaging in a non-contact manner the corneal portion of the eye E. The optical systems include an illumination optical system 10 and a light-receiving optical system 30. The illumination optical system 10 irradiates a cornea with an illumination light flux from an illumination light source 12. The light-receiving optical system 30 receives a reflected light flux from the cornea including a corneal endothelial cell on a light detector (an imaging device 44) to obtain a corneal endothelial cell image.

An optical axis L2 of the illumination optical system 10 and an optical axis L3 of the light-receiving optical system 30 are preliminarily adjusted to intersect each other, for example, on the examinee's eye. For example, the optical systems of this apparatus are configured as those of a general specular microscope (a corneal endothelial cell photographing apparatus). Specifically, the illumination optical system 10 irradiates the cornea with light in an oblique direction. On the other hand, the light-receiving optical system 30 receives reflected light in a specular direction of the cornea. The illumination optical system 10 (the optical axis L2) and the light-receiving optical system 30 (the optical axis L3) are preferred to be symmetrically arranged with respect to a predetermined central axis (such as an observation optical axis L1 described below).

A driving unit 6 is provided to adjust a relative position between a photographing unit (the main unit) 4 and the examinee's eye E. The driving unit 6 is, for example, a well-known alignment drive mechanism. This alignment drive mechanism includes a motor and a slide mechanism, and moves the photographing unit 4 with respect to the eye E in the X-, Y-, and Z-directions.
<Fixation Optical System>

The photographing unit 4 includes fixation optical systems 70 and 75 for guiding a fixation direction of the examinee's eye E. The fixation optical systems 70 and 75 include a plurality of fixation lamps (visible light sources (fixation light sources) 71a to 71i) on a surface perpendicular to the optical axis to change the direction of the visual line of the eye. The fixation optical system 70 is an internal fixation optical system 70 disposed inside of the photographing unit 4. This internal fixation optical system 70 includes a plurality of fixation lamps for guiding the fixation direction of the examinee's eye. On the other hand, the fixation optical system 75 is an external fixation optical system on a housing surface at the examinee's side of the photographing unit 4.

The above-described fixation optical systems 70 and 75 may be configured to move a single fixation lamp to a direction perpendicular to the optical axis. The fixation optical systems 70 and 75 may include a display panel such as a liquid crystal display and organic EL (electroluminescence). A light-emitting position on this display panel is controlled to change the direction of the visual line of the eye.

The internal fixation optical system 70 (70a to 70i) is disposed, for example, to change the direction of the visual line of the examinee's eye E so as to set a photographing position on the cornea in the corneal center and several portions near the corneal center.

The plurality of fixation lamps includes a center fixation lamp (such as a visible light source 71a) and a plurality of adjacent fixation lamps (such as visible light sources 71b to 71i). The fixation lamps may be each, for example, an LED that emits a visually perceivable light (a visible light). The center fixation lamp 71a is a light source to obtain the endothelial image of the corneal central portion. That is, the light emitted from the center fixation lamp guides the eye E in a front direction. This fixation lamp is arranged adjacent to a fixation light axis L4 (at a position to obtain the endothelial image of the central portion, and its location is set by an experiment or a simulation). On the other hand, the adjacent fixation lamps (such as the visible light sources 71b to 71i) are used for obtaining an endothelial image (such as an endothelial image on a circumference with a diameter of 1 to 2 mm (such as 1.3 mm) centered at the corneal center) at a proximity of the corneal center. The plurality of adjacent fixation lamps (such as the visible light sources 71b to 71i) are arranged to have a relationship where a visual axis of the eye E is inclined to the center fixation lamp (the optical axis) at 3 to 10 degrees (preferably, 4 to 6 degrees). In this embodiment, the plurality of adjacent fixation lamps are arranged to have a relationship where the visual axis of the eye E is inclined to the fixation light axis L4 at 5 degrees.

The plurality of fixation lamps 71*a* to 71*i* are arranged, for example, on the same circumference centered at the fixation light axis L4. In other words, the fixation lamps 71*a* to 71*i* are arranged every predetermined angle (for example, every 45 degrees) with respect to viewing from the examinee. The adjacent fixation lamps 71*b* to 71*i*, which are arranged inside of the apparatus 100, incline the eye E at a constant rate with respect to the front direction.

<Alignment-Detecting Sensors>

This apparatus 100 includes alignment-detecting sensors 80 and 85 for detecting an alignment state of the photographing unit with respect to the eye E. The alignment-detecting sensor detects at least any of alignment states in the X-, Y-, and Z-directions with respect to the eye E.

An alignment-detecting sensor for the X- and Y-directions employs, for example, an anterior segment imaging optical system (80) that takes an anterior segment image of the eye E using an imaging device (84). A controller 90 detects an alignment state of the photographing unit with respect to the eye E based on a captured image output from the imaging device (84). Specifically, the controller 90 processes the captured image to detect a deviation between a detecting position of a corneal raster image formed on the anterior segment or a feature portion (such as a pupil and an iris) of the anterior segment and a proper alignment position. This detects an alignment state in the X- and Y-directions. The alignment-detecting sensor for the X- and Y-directions may be, for example, a position sensor (PSD). In this case, the controller 90 detects positional information in the X-direction and positional information in the Y direction that are output from the PSD to detect the alignment state of the photographing unit with respect to the eye E.

As alignment-detecting sensors (80 and 85) for the Z-direction, a Z-detecting optical system is used. The Z-detecting optical system includes, for example, a light-projecting optical system (85*a*) that projects a light flux for detection to the cornea in an oblique direction and a light-receiving optical system (85*b*) where a corneal reflected light flux from the light-projecting optical system is received on a light receiving device. When a line sensor is used as the light receiving device, the controller 90 detects a deviation between a light receiving position of alignment light and a proper alignment position on the line sensor to detect an alignment deviation in the Z-direction. The alignment-detecting sensor for the Z-direction employs, for example, the anterior segment imaging optical system (80) that takes an anterior segment image of the eye E using the imaging device (84). The controller 90 detects an alignment state of the photographing unit 4 with respect to the eye E based on the captured image output from the imaging device (84). The controller 90 processes the captured image to detect the alignment state in the Z-direction depending on whether or not a distance between at least two corneal raster images formed on the anterior segment corresponds to a proper distance.

<Control System>

The calculation controller (hereinafter referred to as the controller) 90 performs a control process of the respective components, an image process, an arithmetic process, and other processes of the apparatus 100. For example, the controller 90 is coupled to the illumination optical system 10, the light-receiving optical system 30, the fixation optical systems 70 and 75, the alignment-detecting sensors 80 and 85, and the monitor 95.

A memory 92 is a storage unit, and stores endothelial images, information of a plurality of fixation positions in a continuous photographing mode, and the like. The memory 92 employs, for example, a semiconductor memory, a magnetic storage device, an optical storage device, or the like.

An operation input unit 96 is an input device operated by an examiner. The operation input unit 96 employs, for example, a pointing device such as a switch, a keyboard, a computer mouse, and a touchscreen.

The monitor 95 is used as an output device, and controlled by the controller 90. The controller 90 displays the obtained endothelial image, a fixation position setting screen, and the like on the monitor 95.

<XYZ Auto Alignment, Auto Tracking, and Auto Shot>

In the case where the detection results of the alignment-detecting sensors 80 and 85 related to the alignment state of the photographing unit 4 with respect to the eye E are out of a predetermined alignment allowable range, the controller 90 controls the driving unit 6 to move the photographing unit 4 to a proper alignment position (automatic alignment) or return the photographing unit 4 to a proper alignment position (automatic tracking). That is, the controller 90 controls the driving unit based on the detection results of the alignment-detecting sensors 80 and 85 in the X- and Y-directions to move the photographing unit 4 with respect to the eye E in the X- and Y-directions. Thus, the controller 90 controls the driving unit 6 based on the detection results of the alignment-detecting sensors 80 and 85 in the Z-direction to move the photographing unit 4 with respect to the eye E in the Z-direction.

In the case where the detection results of the alignment-detecting sensors 80 and 85 satisfy the alignment allowable range, the controller 90 allows the illumination light source 12 to emit light. Subsequently, the controller 90 allows the imaging device 44 to obtain at least one endothelial image. The obtained endothelial image is stored in the memory 92. This sequence of imaging processes by the controller 90 is referred to as an "auto shot". Alternatively, when a plurality of endothelial images are obtained, the controller 90 may control driving of the driving unit 6 to move the photographing unit 4 in a predetermined direction while performing continuous emission of the illumination light source 12 so as to obtain a plurality of endothelial images by the imaging device 44.

<Display and Analysis of the Endothelial Image>

The controller 90 displays at least one obtained endothelial image on the monitor 95. Additionally, the controller 90 analyzes an endothelial cell of the eye E based on the obtained endothelial image. This analysis process is performed based on an operation signal by examiner's operation of a predetermined switch on the operating unit (the operation input unit) 96. For example, the controller 90 calculates at least one of the density of endothelial cells, the size of the cells, a variation in size thereof, and the number of hexagonal cells in a partial image that forms a captured image.

<Integrated Display>

Figure 14:
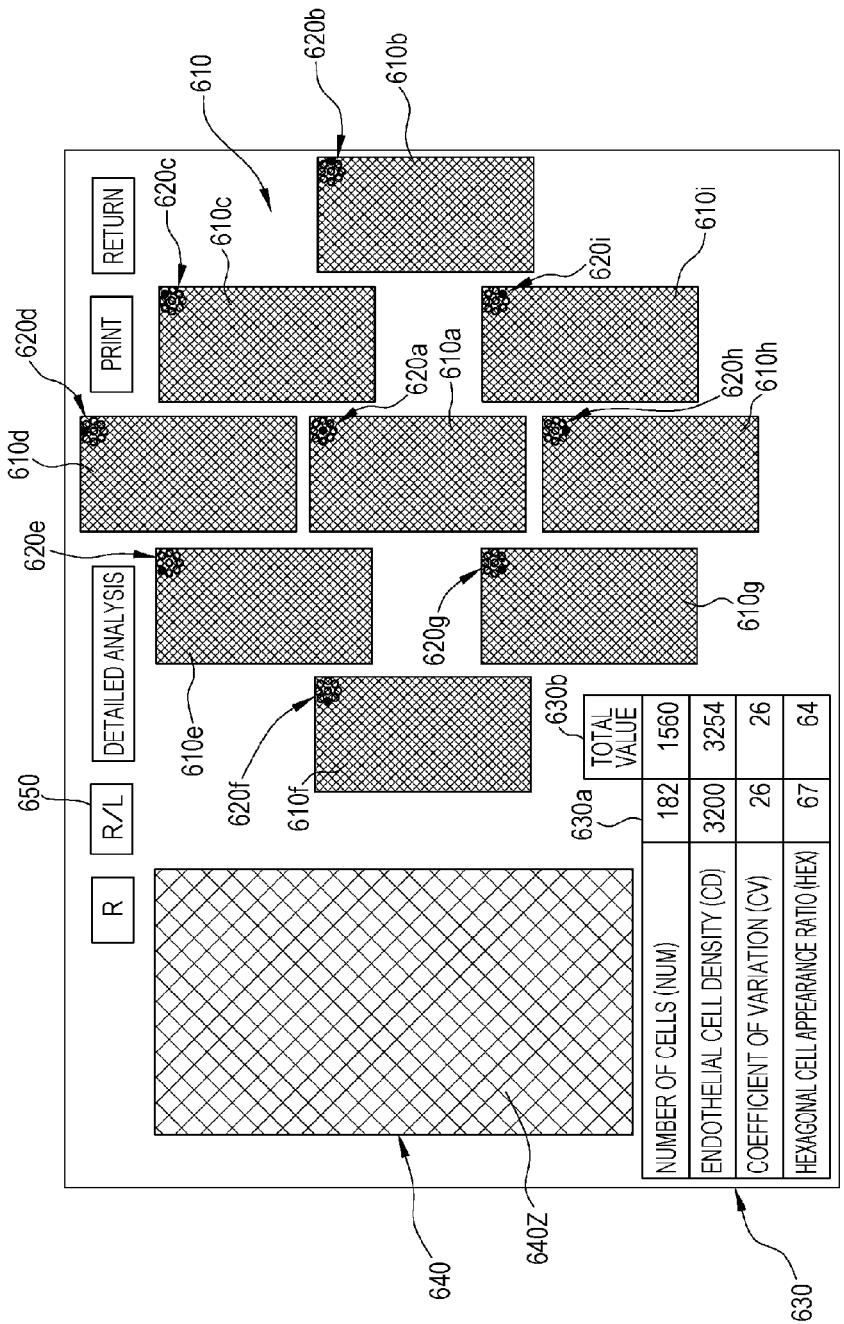
FIG. 14 is a diagram illustrating an example of an integrated display screen according to the present embodiment.

The control unit (serving as a display control unit) 90 simultaneously displays a plurality of endothelial images (endothelial cell images) 610*a* to 610*i*, which are photographed at different positions on the cornea of the examinee's eye, on the monitor 95 with reference to an endothelial cell image photographed at the corneal central portion as a reference position (see FIG. 14). On the same screen, the control unit 90 also displays analysis results 630*a* and 630*b* for the endothelial cell images on the monitor 95 (see FIG. 14).

Figure 15:
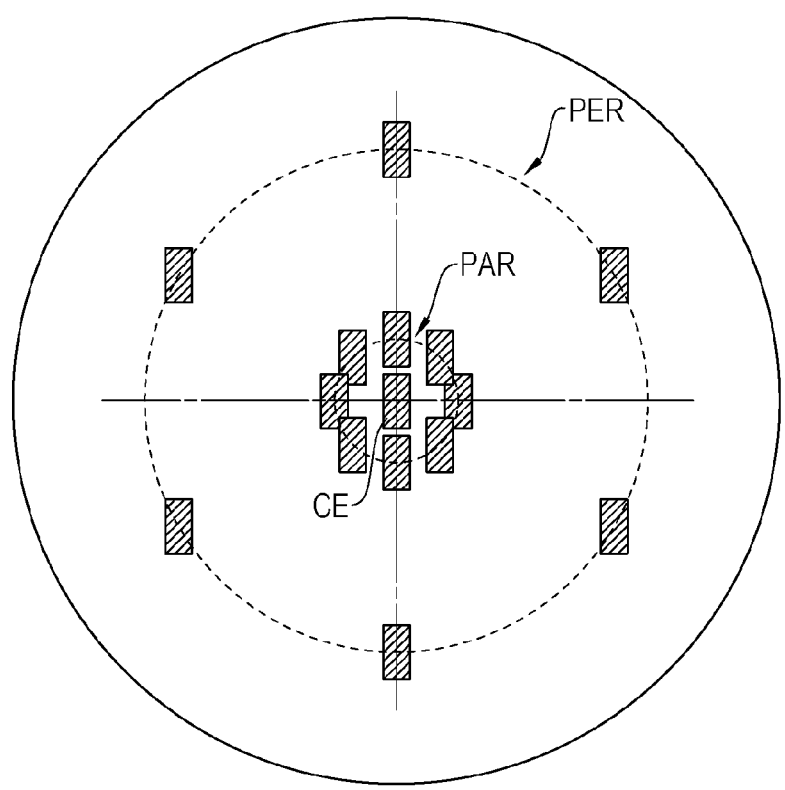
FIG. 15 is a diagram illustrating an example of the positional relationship between a corneal central portion, a region adjacent to the corneal central portion, and a cornea peripheral region on the cornea.

For example, the control unit 90 simultaneously displays the endothelial image 610*a* photographed at the corneal central portion and the endothelial images 610*b* to 610*i* photographed at a plurality of positions in a region adjacent to the corneal central portion on the monitor 95 (see FIGS. 14 and 15).

Selectively or additionally, for example, the control unit 90 simultaneously displays the endothelial image obtained at the corneal central portion and a plurality of endothelial images obtained at a plurality of positions in a peripheral region of the cornea on the monitor 95.

The control unit 90 may arrange the endothelial images displayed on the monitor 95 apart from one another (see FIG. 14). However, it is not limited thereto. The control unit 90 may arrange the endothelial images on the monitor 95 such that the endothelial images displayed on the monitor 95 are at least partly overlapped with one another.

The control unit 90 can display at least one of the endothelial images on the monitor 95 in a magnified manner relative to the other endothelial images (see a magnified image 640Z in FIG. 14). Simultaneously, the control unit 90 may display the analysis result 630a for the magnified endothelial image on the monitor 95.

The control unit 90 may allocate, to the endothelial images 610a to 610i, position displays 620a to 620i (or a symbol display 700 illustrated in FIGS. 16A and 16B) indicating their corresponding positions on the cornea of the examinee's eye. The position displays 620a to 620i may be symbol displays or letters of the alphabet or the like. A method for indicating the positions of the respective endothelial images may be, for example, a method for indicating the fixation position or the photographing position on the cornea.

Here, in the case of obtaining the endothelial images at different positions on the cornea of the examinee's eye, a means for changing a photographing position is used. The means for changing a photographing position has a role of changing the endothelial cell photographing position on the cornea in vertical and horizontal directions. The means for changing a photographing position may be provided as a photographing position changing unit having a plurality of components. For example, as the photographing position changing unit, a fixation optical system (see, for example, the fixation optical system 70 or the fixation optical system 75) is used. The fixation optical system includes a plurality of sight fixation lights and can change the line of sight of the examinee's eye. A drive unit (see the drive unit 6, for example) may function as the photographing position changing unit. Thus, the drive unit may be used as the means for changing a photographing position. The drive unit can move the illuminating optical system and the light receiving optical system in the vertical and horizontal directions with respect to the examinee's eye. The drive unit may be configured to rotationally move the illuminating optical system and the light receiving optical system in the vertical and horizontal directions with respect to the examinee's eye. The means for changing a photographing position may also be configured to change the photographing position by using the fixation optical system and the drive unit in combination. When the optical axis of the illuminating optical system 10 and the optical axis of the light receiving optical system 30 are symmetrically disposed with respect to the observation optical axis L1 (see FIG. 2), for example, the photographing position on the cornea is the position at which the optical axis of the illuminating optical system 10 and the optical axis of the light receiving optical system 30 intersect with each other.

The apparatus 100 according to the present embodiment includes an image processing means (image processor) that processes a photographed endothelial image and acquires an analysis result regarding the endothelial cells of the examinee's eye. The control unit 90 also provides the role of the image processing means. However, it is not limited thereto. The apparatus 100 may be provided with a separate image processor.

<Continuous Photographing Mode>

Hereinafter, a description will be given of a process of a continuous photographing mode for continuously obtaining endothelial images at a plurality of photographing positions using a plurality of fixation lamps (the visible light sources (the fixation light sources) 71a to 71i).

<Fixation Position Setting>

FIG. 10 is a diagram illustrating an exemplary fixation position setting screen displayed on the monitor 95. On the fixation position setting screen, illumination positions and an illumination order of the fixation lamps in the continuous photographing mode are preliminarily set. The controller 90 controls the fixation position in the continuous photographing mode based on the illumination positions and the illumination order of the set fixation lamps.

For example, the illumination positions and illumination order of the fixation lamps are preliminarily set by the examiner and stored in the memory 92 as data. During the examination, the controller 90 controls the fixation position in the continuous photographing mode based on the data stored in the memory 92.

A fixation lamp group where the illumination positions and the illumination orders of the fixation lamps are set may be preliminarily stored in the memory 92. The controller 90 can use this fixation lamp group in the continuous photographing mode. For example, in order to select a plurality of groups as needed, a plurality of fixation lamp groups may be stored in the memory 92. The fixation lamp group includes, for example, a fixation target group set for taking endothelial images in an upper portion/a lower portion/a left portion/a right portion of the cornea in addition to the corneal central portion and a fixation target group set for taking endothelial images in an upper right portion/a lower right portion/a lower left portion/an upper left portion of the cornea in addition to the corneal central portion. When any one of fixation target groups is selected, the fixation lamps are lighted in accordance with a predetermined order. For example, as a lighting procedure, for example, the light source 71a is lighted, and then a light source (any of the light sources 71b to 71i) for taking an endothelial image in the peripheral portion is lighted. At this time, for example, the light source at the adjacent fixation position is sequentially lighted (for example, clockwise or counterclockwise). The lighting procedure is not limited to the orders described above. Additionally, an illumination order of the fixation lamps in any fixation lamp group may be arbitrarily set.

<Photographing Operation>

The controller 90 controls the illumination optical system 10 and the light-receiving optical system 30 to obtain an endothelial image at a preliminarily set first fixation position. The examiner or the controller 90 determines propriety of the endothelial image obtained at the first fixation position. Corresponding to the obtained determination result, the controller 90 lights a fixation lamp corresponding to a second fixation position, and allows the photographing unit 4 to obtain an image at the second fixation position. That is, the controller 90 controls the illumination optical system 10 and the light-receiving optical system 30 to allow the photographing unit 4 to take an endothelial image at the second fixation position. The propriety of the endothelial image is determined by input from the examiner or the controller 90.

For example, the controller 90 presents the fixation lamp corresponding to the preliminarily set first fixation position and controls the illumination optical system 10 and the light-receiving optical system 30 to obtain an endothelial image at the first fixation position. The controller 90 displays the endothelial image obtained at the first fixation position on the monitor 95.

The examiner confirms the endothelial image at the first fixation position displayed on the monitor 95. Subsequently, the examiner inputs an operation signal for transition to a photographing position at the preliminarily set next fixation position to the controller 90 from the operation input unit 96 in a state where the endothelial image is displayed on the monitor 95. Corresponding to this input signal, the controller 90 presents a fixation lamp corresponding to the preliminarily set second fixation position on the monitor 95. Subsequently, the controller 90 allows the photographing unit 4 to obtain an image in the second fixation position while controlling the illumination optical system 10 and the light-receiving optical system 30. As a result, the photographing unit 4 obtains an endothelial image at the second fixation position. Subsequently, the controller 90 displays the endothelial image obtained at the second fixation position on the monitor.

As described above, the controller 90 switches the illuminated position of the fixation lamp to the next position based on the illumination positions and the illumination orders of the plurality of fixation lamps stored in the memory 92 triggered by the operation signal for transition to photographing at the preliminarily set next fixation position. When the fixation position is switched, the controller 90 allows obtaining an image at the next fixation position to obtain an endothelial image at the next fixation position. Thus, the endothelial image at each fixation position (the first fixation position, the second fixation position, the third fixation position, . . . in this order) is sequentially obtained. Accordingly, the examiner smoothly moves to the obtainment of the endothelial image at the next photographing position after confirming the obtained endothelial image.

As already described, the controller 90 allows automatic tracking in the case where the detection results of the alignment-detecting sensors 80 and 85 related to the alignment state of the photographing unit 4 with respect to the eye E deviates from the allowable range of alignment. In the case where obtaining an image at the next fixation position is allowed and the detection results of the alignment-detecting sensors 80 and 85 satisfy the alignment allowable range, the controller 90 lights the illumination light source 12 to start obtaining an endothelial image at the next fixation position. This allows the photographing unit 4 to perform photographing at the next fixation position more smoothly.

More preferably, the controller 90 may perform automatic tracking from a previous step where the operation signal for transition to photographing at the preliminarily set next fixation position is input. In this case, the photographing unit 4 moves to the obtainment of the next endothelial image in a short time when photographing is allowed by switching to the next fixation position.

The controller 90 may be set to light a fixation lamp corresponding to the next fixation position in the case where the propriety of the obtained endothelial image is determined as proper by a determination process. The controller 90 may determine the propriety of the endothelial image based on, for example, image quality of the endothelial image and an alignment deviation amount when the endothelial image is obtained.

The controller 90 may display a photographing position display (such as a fixation position display 500) on the monitor 95. For example, the controller 90 displays a current photographing position, a plurality of preliminarily set photographing positions, non-set photographing positions in a determinable state (for example, in a color-coded manner) on the monitor 95.

Embodiment

Hereinafter, an exemplary apparatus according to this embodiment will be described with reference to the accompanying drawings. FIG. 1 is a side view schematically illustrating a configuration of a corneal endothelial cell photographing apparatus according to this embodiment.

This apparatus 100 is what is called a stationary apparatus. This apparatus 100 includes a base 1, a head support unit 2 mounted on the base 1, a movable table 3 movably disposed on the base 1, and a photographing unit (the main unit) 4 movably disposed with respect to the movable table 3. The photographing unit 4 includes a monitor 95. The movable table 3 can move in the X- and Z-directions on the base 1 by operation of a joystick 5.

The photographing unit 4 includes the monitor 95. The movable table 3 can move in the X- and Z-directions on the base 1 by operation of the joystick 5. That is, the photographing unit 4 is moved, by a XYZ driving unit 6 disposed in the movable table 3, in a right-and-left direction (X-direction), up-and-down direction (Y direction), and back-and-forth direction (Z-direction) with respect to an examinee's eye E. The movable table 3 is moved in the X- and Z-directions on the base 1 by operation of the joystick 5. Further, when an examiner rotates a rotation knob 5a, the photographing unit 4 is moved in the Y direction by Y-drive of the XYZ driving unit 6. At a top of the joystick 5, a start switch 5b is disposed. The start switch 5b is a switch to start an examination by the apparatus 100. For example, in the case of an examination by an automatic examination program, the start switch 5b functions as a program start switch. The display monitor 95 is disposed on an examiner side of the photographing unit 4. In this embodiment, the photographing unit 4 is moved relative to the eye E by a sliding mechanism (not shown) and the XYZ driving unit 6.

Instead of disposing the mechanical sliding mechanism, driving of the motor of the driving unit 6 may allow the photographing unit 4 to move with respect to right and left eyes. The manual operating member of this apparatus 100 is not limited to the joystick 5, and may be a touchscreen.

Figure 3:
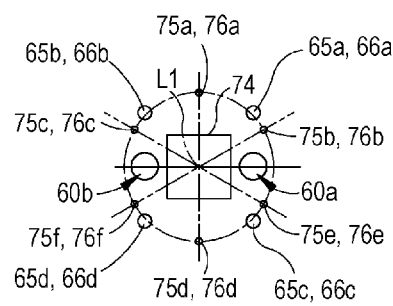
FIG. 3 is an explanatory view when a first projecting optical system and a second projecting optical system in the corneal endothelial cell photographing apparatus are viewed from an examinee's side.

FIG. 2 is a schematic diagram exemplarily illustrating an optical arrangement of the optical systems stored in the photographing unit 4 as viewed from top and a schematic configuration of the control system. FIG. 3 is an explanatory view where a first projecting optical system and a second projecting optical system are viewed from an examinee's side. The optical systems include an illumination optical system 10, an imaging optical system (a light-receiving optical system) 30, a front projecting optical system 50, first projecting optical systems 60a and 60b, second projecting optical systems 65a to 65d (see FIG. 3), internal fixation optical systems 70 (70a to 70g), external fixation optical systems 75 (75a to 75f), an anterior segment observing optical system 80, and a Z alignment detecting optical system 85.

The illumination optical system 10 irradiates a cornea Ec with an illumination light from an illumination light source 12 in an oblique direction. The illumination optical system 10 includes the illumination light source (such as a visible LED and a flash lamp) 12 that emits a visible light for endothelium photographing, a condenser lens 14, a slit plate 16, a dichroic mirror 18 that reflects visible light but transmits infrared light, and a light projection lens 20. Light emitted from the illumination light source 12 irradiates the slit plate 16 through the condenser lens 14. The slit light having passed through the slit plate 16 is converged by the light projection lens 20 via the dichroic mirror 18 and then irradiates a cornea. Here, the slit plate 16 and the cornea Ec are arranged at respective positions approximately conjugated with each other with respect to the light projection lens 20.

The imaging optical system 30 receives reflected light from the cornea Ec including endothelial cells on an imaging device 44 so as to obtain an endothelial cell image. The imaging optical system 30 is symmetric to the illumination optical system 10 with respect to an optical axis L1. The imaging optical system 30 includes an objective lens 32, a dichroic mirror 34 that reflects visible light but transmits infrared light, a mask 35, a first image forming lens 36, a total reflection mirror 38, a second image forming lens 42, and a first two-dimensional imaging device (such as a two-dimensional charge coupled device image sensor, and a two dimensional complementary metal oxide semiconductor image sensor) 44 that is specifically designed to obtain cell images. The mask 35 is arranged at a position to be approximately conjugated with the cornea Ec with respect to the objective lens 32. An image-forming optical system, which forms an endothelial image on the imaging device 44, is formed by the first image forming lens 36 and the second image forming lens 42. This imaging device 44 is placed at a position to be approximately conjugated with the cornea Ec with respect to a lens system of the imaging optical system 30.

Cornea-reflected light generated by the illumination optical system 10 travels along an optical axis L3 direction (an oblique direction). This reflected light is converged by the objective lens 32, and then reflected by the dichroic mirror 34. Furthermore, the reflected light once forms an image on the mask 35. The mask 35 shields a light that becomes noise when an endothelial cell image is obtained. Light passed through the mask 35 forms an image on the two-dimensional imaging device 44 via the first image forming lens 36, the total reflection mirror 38, and the second image forming lens 42. As a result, a corneal endothelial cell image at a high magnification is obtained. An output terminal of the imaging device 44 is coupled to a controller 90. Via this output terminal, the obtained cell image is stored in the memory 92 through the controller 90 from the imaging device 44. The controller 90 displays the cell image on the monitor 95.

The front projecting optical system 50 projects an alignment target toward the cornea Ec from front. The front projecting optical system 50 includes an infrared light source 51, a light projection lens 53, and a half mirror 55. The front projecting optical system 50 projects infrared light for XY alignment detection to the cornea Ec from a direction of the observation optical axis L1. Infrared light emitted from the light source 51 is converted into parallel light flux by the light projection lens 53 and then reflected by the half mirror 55. Furthermore, the reflected light is projected onto the corneal central portion of the cornea Ec to form a target i10 (see FIG. 4B).

The first projecting optical systems 60a and 60b project infinite alignment targets toward the cornea Ec in oblique directions. The first projecting optical systems 60a and 60b are inclined at respective predetermined angles to the optical axis L1. The first projecting optical systems 60a and 60b respectively include infrared light sources 61a and 61b and collimator lenses 63a and 63b. Additionally, the first projecting optical systems 60a and 60b are arranged bilaterally symmetric with respect to the optical axis L1 to project infinite targets to the eye E (see FIG. 2). Here, the first projecting optical systems 60a and 60b are symmetric with respect to the optical axis L1, and arranged on approximately the same meridian line as the horizontal direction perpendicular to the optical axis L1 (see FIG. 3).

Figure 4A:
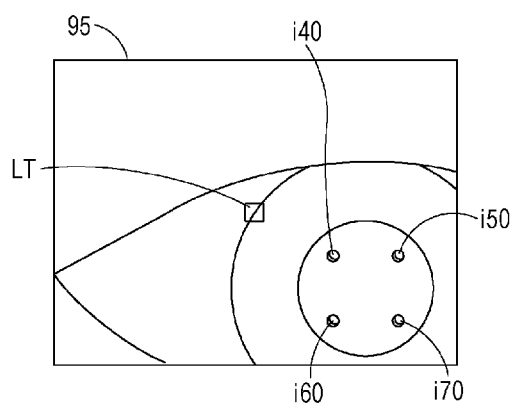
FIGS. 4A and 4B are diagrams illustrating exemplary anterior segment observation screens on a monitor in the case where an endothelium of a corneal central portion is imaged.
Figure 4B:
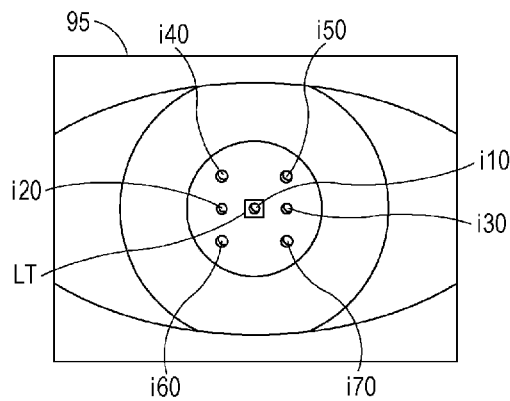

Light emitted from the light source 61a and light emitted from the light source 61b are respectively collimated by the collimator lenses 63a and 63b and then projected onto the cornea Ec to form targets i20 and i30 (see FIG. 4B).

The second projecting optical systems 65a to 65d respectively project finite alignment targets toward the cornea Ec in oblique directions. The second projecting optical systems 65a to 65d are respectively inclined with respect to the optical axis L1. The second projecting optical systems 65a to 65d include infrared light sources 66a to 66d, respectively. The second projecting optical systems 65a to 65d are arranged symmetrically with respect to the optical axis L1 to project finite targets onto the eye E. Here, the second projecting optical systems 65a and 65b are arranged above the optical axis L1 and at the same height in the Y-direction. The second projecting optical systems 65c and 65d are arranged below the optical axis L1 and at the same height in the Y-direction. The second projecting optical systems 65a and 65b are vertically symmetrical to the second projecting optical systems 65c and 65d with respect to the optical axis L1.

Herein, light from the light source 66a and light from the light source 66b are irradiated to an upper portion of the cornea Ec from upper oblique directions, respectively. As a result, targets i40 and i50 that are virtual images of the light sources 66a and 66b are formed on the cornea Ec. Light from the light source 66c and light from the light source 66d are irradiated to a lower portion of the cornea Ec from lower oblique directions, respectively. As a result, targets i60 and i70 that are virtual images of the light sources 66c and 66d are formed on the cornea Ec (see FIGS. 4A and 4B).

According to the target projecting optical system above, the target i10 is formed at a corneal apex of the eye E (see FIG. 4B). The targets i20 and i30, which are provided by the first projecting optical systems 60a and 60b, are formed at the same horizontal positions as that of the target i10 and bilaterally symmetric with respect to the target i10. Furthermore, the targets i40 and i50, which are provided by the second projecting optical systems 65a and 65b, are formed above the target i10 and bilaterally symmetric with respect to the target i10. The targets i60 and i70, which are provided by the second projecting optical systems 65c and 65d, are formed below the target i10 and bilaterally symmetric with respect to the target i10.

The internal fixation optical systems 70a to 70i project fixation targets onto the eye E from inside. The internal fixation optical systems 70a to 70i include visible light sources (fixation lamps) 71a to 71i, a light projection lens 73, and a dichroic mirror 74 that reflects visible light but transmits infrared light. Visible light emitted from the light source 71 is converted into parallel light flux by the light projection lens 73. Subsequently, the light is reflected by the dichroic mirror 74 and projected onto a fundus of the eye E. An external fixation optical system is arranged near the first projecting optical systems 60a and 60b and the second projecting optical systems 65a to 65d described above.

The internal fixation optical systems 70a to 70i each include a fixation target. These fixation targets are arranged at different positions along a direction perpendicular to an optical axis L4, and guide the fixation direction of the eye E to each direction. The internal fixation optical systems 70a to 70i are disposed inside of the photographing unit 4. For example, the visible light source 71a is arranged near the optical axis L4. When an endothelial image of the corneal central portion is obtained by the photographing unit 4, the visible light source 71a is used to guide the eye E to the front direction. A plurality of visible light sources 71b to 71i are arranged on the same circumference centered on the optical axis L4. These visible light sources 71b to 71i are arranged at predetermined angular intervals when seen from an examinee's side. For example, as illustrated in FIG. 2, the visible light sources 71b to 71i are arranged, with respect to the visible light source 71a, at respective positions at 0 degree, 45 degrees, 90 degrees, 135 degrees, 180 degrees, 225 degrees, 270 degrees, and 315 degrees for each increment of 45 degrees. When the photographing unit 4 obtains an endothelial image around the corneal center, the visible light sources 71b to 71i guide the direction of the visual line of the eye E to the circumferential direction.

The external fixation optical systems 75a to 75f project fixation targets from outside. The external fixation optical systems 75a to 75f have a plurality of fixation targets arranged at different positions in the X- and Y-directions. The external fixation optical systems 75a to 75f change the fixation direction of the examinee's eye at a larger angle than that of the internal fixation optical system 70 using the fixation targets. The external fixation optical systems 75a to 75f are disposed outside of the photographing unit 4 at the eye E side. For example, the external fixation optical systems 75a to 75f include visible light sources (fixation lamps) 76a to 76f. These visible light sources 76a to 76f are arranged on the same circumference centered on the optical axis L1. For example, the visible light sources 76a to 76f are arranged, with respect to the optical axis L1, at 2, 4, 6, 8, 10, and 12-o'clock positions, respectively, when seen from the examinee. The visible light sources 76a to 76f are used to guide the direction of the visual line of the eye E to the circumferential direction when the endothelial image of the peripheral portion of the cornea is obtained by the photographing unit 4. In this case, an endothelial cell image further outside of the image obtained by the visible light sources 71b to 71i is obtained.

For example, when a lower portion of the cornea is photographed, the position of the fixation lamp (fixation target) is set to an upper side to guide the fixation of the eye E in an upward direction. When an upper portion of the cornea is photographed, the position of the fixation lamp (fixation target) is set to a lower side to guide the fixation of the eye E in a downward direction.

Next, returning to FIG. 2, the anterior segment observing optical system 80 will be described. The anterior segment observing optical system 80 observes an anterior segment image from front. The anterior segment observing optical system 80 includes an objective lens 82 and a two-dimensional imaging device 84 to obtain an anterior segment front image. That is, the anterior segment observing optical system 80 includes the second two-dimensional imaging device 84 that is different from the first imaging device 44, and takes an anterior segment image and an alignment target by the two-dimensional imaging device 84. The two-dimensional imaging device 84 employs, for example, a two-dimensional CCD image sensor and a two-dimensional CMOS image sensor. In the anterior segment observing optical system 80, a virtual light beam representing the light flux that passes through the entire system is denoted by the optical axis L1.

The anterior segment illuminated by an anterior segment illumination light source (not shown) is imaged by the two-dimensional imaging device 84 through the external fixation optical system (dichroic mirror) 75, the half mirror 55, and the objective lens 82. Similarly, a corneal reflection image formed by the front projecting optical system 50, the first projecting optical systems 60a and 60b, and the second projecting optical systems 65a to 65d is received on the two-dimensional imaging device 84.

An output terminal of the imaging device 84 is coupled to the controller 90. Thus, as illustrated in FIGS. 4A and 4B, the monitor 95 displays the anterior segment image taken by the imaging device 84 through the controller 90. A reticle LT electronically displayed on the monitor 95 represents a reference for XY alignment. The observing optical system 80 doubles as a detecting optical system for detecting an alignment state of the photographing unit 4 with respect to the eye E.

The Z alignment detecting optical system 85 detects the alignment state of the photographing unit 4 in the Z direction with respect to the eye E. The Z alignment detecting optical system 85 includes a light-projecting optical system 85a and a light-receiving optical system 85b. The light-projecting optical system 85a projects a detection light flux to the cornea Ec in an oblique direction. The light-receiving optical system 85b receives a corneal reflected light flux generated by the light-projecting optical system 85a. The optical axis L2 of the light-projecting optical system 85a and the optical axis L3 of the light-receiving optical system 85b are arranged bilaterally symmetric with respect to the observation optical axis L1.

The light-projecting optical system 85a includes, for example, an illumination light source 86 that emits infrared light, a condenser lens 87, a pin-hole plate 88, and the lens 20. Here, the pin-hole plate 88 and the cornea Ec are arranged at positions approximately conjugated with each other with respect to the lens 20. The light-receiving optical system 85b includes, for example, the lens 32 and a one-dimensional light receiving device (a line sensor) 89. Here, the one-dimensional light receiving device 89 and the cornea Ec are arranged at positions approximately conjugated with each other with respect to the lens 32.

Infrared light emitted from the light source 86 illuminates the pin-hole plate 88 through the condenser lens 87. Light having passed through an opening of the pin-hole plate 88 is projected to the cornea Ec through the lens 20. Corneal reflected light is then received on the light receiving device 89 through the lens 32 and the dichroic mirror 34.

An output terminal of the light receiving device 89 is coupled to the controller 90. Accordingly, the light receiving device 89 is used for Z alignment detection with respect to the eye E by the controller 90. Here, an alignment light flux is received on the light receiving device 89. At this time, a position of the alignment light flux on the light receiving device 89 changes depending on a positional relationship between the photographing unit 4 and the eye E in the Z direction. This change is detected by the controller 90. For example, the controller 90 detects the position of corneal reflected light based on a detection signal from the light receiving device 89 to detect the alignment state in the Z direction. The alignment detection using the light receiving device 89 is utilized for accurate alignment of the photographing unit 4 with respect to the eye E.

The controller 90 controls the entire apparatus 100. The controller 90 is coupled to the rotation knob 5a, the start switch 5b, the XYZ driving unit 6, the two-dimensional imaging devices 44 and 84, the respective light sources, the storage device (memory) 92, the monitor 95, and the operating unit (the operation input unit) 96. The monitor 95 of this embodiment is a touchscreen that allows input operation from the examiner, and forms at least a part of the operation input unit 96.

The apparatus 100 of this embodiment has two photographing modes. Specifically, in a first photographing mode, the examiner sets the fixation position (an each position photographing mode) for each photographing of the endothelial image. In a second photographing mode, photographing is continuously performed at a plurality of preliminarily set fixation positions (hereinafter referred to as a continuous photographing mode). These photographing modes are switchable. Mode switching is, for example, performed by using a predetermined mode selection switch disposed at the operating unit (the operation input unit) 96 or by parameter setting. This apparatus 100 is not necessary an apparatus having two modes. For example, this apparatus 100 may be an apparatus having the second photographing mode only.

The controller 90 controls display of the monitor 95. Furthermore, the controller 90 detects the alignment state of the photographing unit 4 with respect to the eye E in the X-, Y-, and Z-directions based on the results of receiving light from the alignment targets. The controller 90 outputs a command signal to move the photographing unit 4 to the driving unit 6 based on the detection result. The controller 90 also detects the alignment state of the photographing unit 4 in the Z direction with respect to the eye E based on the light reception result from the light receiving device 89.

In the apparatus 100 thus configured, an alignment operation will be described. FIGS. 4A and 4B are diagrams illustrating exemplary anterior segment observation screens in the case where an endothelium in the corneal central portion is photographed. FIG. 4A illustrates a display example in the case where the photographing unit 4 has an alignment deviation with respect to the eye E. FIG. 4B illustrates a display example in the case where alignment of the photographing unit 4 with respect to the eye E is appropriate.

The alignment of the photographing unit 4 with respect to the eye E is performed as follows. The light source 71 is lighted to guide the fixation direction of the eye E to the front. First, the examiner asks the examinee to gaze the fixation target. While observing the anterior segment image displayed on the monitor 95, the examiner performs alignment of the photographing unit 4 with respect to the eye E.

After rough alignment is performed as above, as illustrated in FIG. 4A, a corneal target formed by diffusion light is detected on a light receiving plane of an imaging device 64. The controller 90 searches for a raster on the image from upper-left coordinate position to the lower right of the screen. When the targets i40, i50, i60, and i70 are detected, the controller 90 determines the respective positions of the detected raster.

The controller 90 then detects the center position of a rectangle formed by the positions of the targets i40, i50, i60, and i70 as approximately a corneal apex. Subsequently, the controller 90 detects an alignment deviation direction/an amount of deviation in the X- and Y-directions with reference to the approximately corneal apex. Based on this detection result, the controller 90 controls driving of the driving unit 6 to move the photographing unit 4 in the X- and Y-directions such that the alignment deviation falls within a predetermined alignment allowable range. This allows automatic alignment in a wide range.

When the photographing unit 4 is moved as above and the target i10 is detected, the controller 90 terminates the alignment using the above-described targets i40 to i70. Subsequently, the controller 90 performs alignment using the target i10. Here, the controller 90 discriminates between the target i10 and the targets i40 to i70 based on their positional relationships.

The controller 90 detects the coordinate position of the target i10 as an approximately corneal apex, and detects the alignment deviation direction/the amount of deviation in the X- and Y-directions. Subsequently, the controller 90 controls driving of the driving unit 6 to move the photographing unit 4 in the X- and Y-directions such that the deviation of the alignment of the photographing unit 4 with respect to the eye E falls within a predetermined alignment allowable range.

When the target i10 is detected as above, similarly, the infinite targets i20 and i30 are detected by the controller 90. Therefore, the controller 90 compares the interval between the infinite targets i20 and i30 detected as above with the interval between the finite targets i60 and i70 to determine the alignment deviation direction/the amount of deviation in the Z direction (first alignment detection). Subsequently, the controller 90 moves the photographing unit 4 in the Z direction such that the alignment deviation in the Z direction falls within a predetermined alignment allowable range (first automatic alignment).

In the case of the first alignment detection, the controller 90 uses the following characteristic when detecting the alignment deviation in the Z direction. That is, in this characteristic, the interval between the infinite targets i20 and i30 changes little when the movable table (a measuring portion) 3 is displaced in an operating distance direction while the image interval between the finite targets i60 and i70 changes (for the details, see JP-A-6-46999). Instead of the targets i60 and i70, the targets i40 and i50 may be used. Alternatively, the Z alignment may be detected based on a distance of the target (target height) from the optical axis L1.

The controller 90 stops operations for the first automatic alignment when determining the alignment state to be proper in the first Z alignment detection. Subsequently, the controller 90 activates a second Z alignment detection using the detecting optical system 85 and a second automatic alignment based on a detection result of the second Z alignment detection.

The controller 90 lights the light source 86 to project alignment light flux to the cornea Ec (the light source 86 may be lighted preliminarily) and also detects the corneal reflected light flux by the light receiving device 89. The controller 90 controls driving of the driving unit 6 based on a light reception result from the light receiving device 89 to move the photographing unit 4 in the Z-direction.

Figure 5:
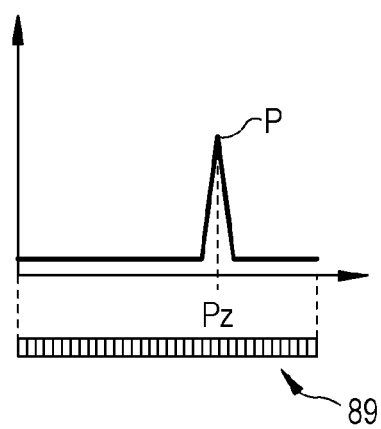
FIG. 5 is a graph illustrating an epithelial peak detected on a line sensor.

For example, the controller 90 detects a peak P corresponding to the reflected light flux from corneal epithelium based on a light receiving signal output from the light receiving device 89, and then detects a position Pz of the epithelial peak on the light receiving device 89 (see FIG. 5). The controller 90 drives the driving unit 6 such that a peak of the light receiving signal by the reflected light flux from the epithelium comes to a predetermined position (such as the center position) on the light receiving device 89.

When the alignment state in the XYZ directions satisfies the alignment completion condition by the above-described alignment operation, the controller 90 determines that the alignment in the XYZ directions of the photographing unit 4 with respect to the eye E is completed properly and then generates a trigger signal.

<Photographing of Endothelial Cells>

Figure 6:
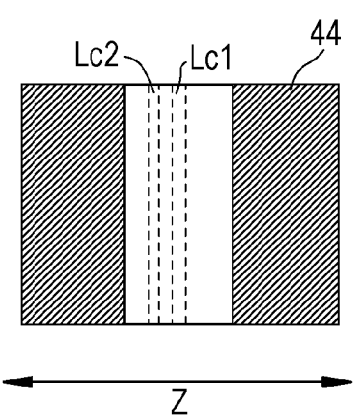
FIG. 6 is an explanatory diagram illustrating one example when a light receiving state of a corneal image is determined based on an output image from an imaging device.

When the controller 90 transmits the trigger signal, the illumination light source 12 continuously lights in response to this trigger signal. The two-dimensional imaging device 44 uses visible illumination light from the illumination light source 12 to obtain a corneal endothelial cell image. At that time, the controller 90 is preferred to light the light source 12 with a light intensity that allows detection of epithelium reflected light but does not allow detection of endothelium reflected light. Subsequently, the controller 90 lights the light source 12 and controls driving of the driving unit 6 to move the photographing unit 4 forward to the eye E. During movement of the photographing unit 4 in the Z direction, the controller 90 continues the automatic alignment operation (tracking control using the imaging device 84) in the X- and Y-directions. The controller 90 detects an output image from the imaging device 44, and controls the light source 12 and the driving unit 6 based on a detection result. FIG. 6 is an explanatory diagram illustrating one example when a light receiving state of a corneal image is determined based on an output image from the imaging device 44. The mask 35 is, as illustrated in FIG. 2, arranged ahead of the imaging device 44. This mask 35 includes, as illustrated in FIG. 6, an opening portion (a white rectangular area in the center) and a light-shielding portion (black hatching on the right and the left).

For example, the controller 90 sets a first detection region Lc1 and a second detection region Lc2 on the imaging device 44 to detect the light receiving state of the corneal image. These regions Lc1 and Lc2 extend in a direction perpendicular to a thickness direction (the Z direction of FIG. 6) of the cornea. The first detection region Lc1 is set to detect a light receiving state of the epithelium reflected light. The second detection region Lc2 is set to detect a light receiving state of the endothelium reflected light. The controller 90 calculates a summed value SLC1 of luminance of respective pixels in the first detection region Lc1. The controller 90 also calculates a summed value SLC2 of luminance of respective pixels in the second detection region Lc2.

Figure 7A:
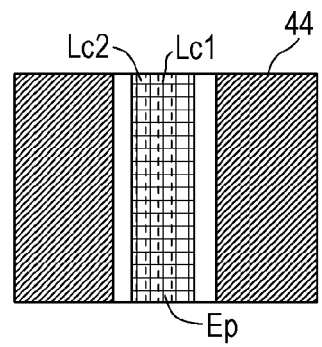
FIGS. 7A to 7C are explanatory diagrams illustrating changes in light receiving state of cornea-reflected light while a photographing unit is moved forward to an eye E.
Figure 7B:
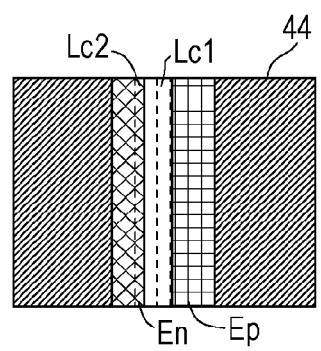
Figure 7C:
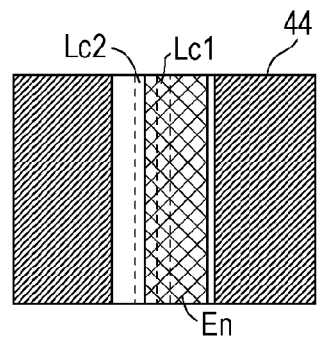
Figure 8A:
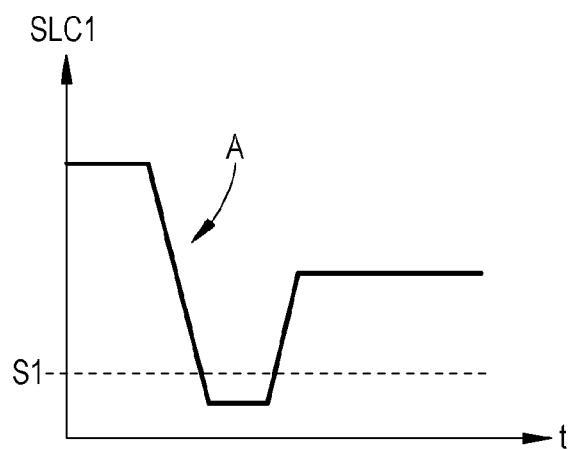
FIGS. 8A and 8B are graphs illustrating changes in summed values SLC1 and SLC2 when the photographing unit is moved forward to the eye E in chronological order.
Figure 8B:
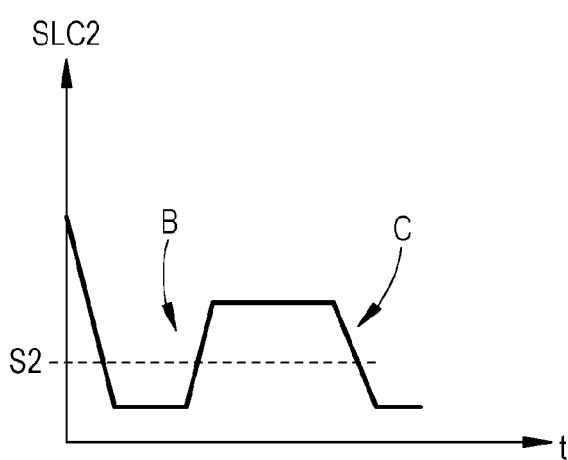

FIGS. 7A to 7C are diagrams illustrating changes in light receiving state of the cornea-reflected light while the photographing unit 4 is moved forward to the eye E. FIGS. 8A and 8B are graphs illustrating changes in the summed values SLC1 and SLC2 in chronological order while the photographing unit 4 is moved forward to the eye E. FIG. 8A corresponds to the summed value SLC1, and FIG. 8B corresponds to the summed value SLC2.

FIG. 7A is a diagram obtained when the alignment in the XYZ directions is completed. At this time, an epithelium reflected light Ep is received on the first detection region Lc1 on the imaging device 44. Therefore, the first summed value SLC1 is calculated to be a high value corresponding to the epithelium reflection (see FIG. 8A).

When the photographing unit 4 is moved forward to the eye E, the epithelium reflected light Ep is moved rightward on the papers of FIGS. 7A to 7C. When the epithelium reflected light Ep goes across the first detection region Lc1 on the imaging device 44, the summed value SLC1 greatly decreases (see FIG. 7B and an inclination A in FIG. 8A). When the summed value SLC1 decreases below a predetermined threshold value S1, the controller 90 increases the light amount of the light source 12 to the degree that an endothelial image appears in the output image from the imaging device 44. Accordingly, the endothelium reflected light En can be detected by the imaging device 44.

After increasing the light amount of the light source 12, the controller 90 continues forward movement of the photographing unit 4 and stores images serially output from the imaging device 44 in the memory 92 as needed. The two-dimensional imaging device 44 outputs imaging signals corresponding to the frame rate to the controller 90 as needed. Thus, the photographing unit 4 obtains a plurality of endothelial picked-up images (for example, about 30 to 40 images) within 1 to 2 seconds. The controller 90 allows the memory 92 to store an image that satisfies a certain condition (for example, an appropriate endothelial cell image has been obtained) among output images as a still image. Thus, the endothelial cell image is photographed. In this case, the controller 90 may preliminarily store a predetermined number of images in the memory 92. Subsequently, the controller 90 outputs the photographed image stored in the memory 92 to the monitor 95.

When the photographing unit 4 is moved forward to the eye E, the endothelium reflected light En is moved rightward in the image (see FIGS. 7A to 7C). When the endothelium reflected light En reaches the second detection region Lc2 on the imaging device 44, the summed value SLC2 increases (see an inclination B in FIG. 8B). While the endothelium reflected light En is received on the second detection region Lc2 on the imaging device 44, a high value is maintained. Furthermore, when the photographing unit 4 is moved further to the eye E and the endothelium reflected light En passes across the detection region Lc2, the summed value SLC2 greatly decreases (see FIG. 7C and an inclination C in FIG. 8B). When the summed value decreases below a predetermined threshold value S2, the controller 90 dims (including turning off) the light source 12 and stops driving of the driving unit 6 to stop the forward movement of the photographing unit 4.

Examples of the technique that continuously lights the light source 12 include a technique of always lighting the light source 12 and a technique of consecutively blinking the light source 12. In the case of consecutively blinking the light source 12, for example, the controller 90 blinks the light source 12 such that a plurality of endothelial images can be obtained during the movement of the photographing unit 4. Further, the light source 12 may be blinked consecutively in synchronization with the frame rate of the two-dimensional imaging device 44. For example, in the case where an imaging time of one image is 30 ms, the controller 90 lights the light source 12 for several milliseconds from the start of image acquisition. Subsequently, the controller 90 turns off the light source 12. When acquisition of a next image is started, the controller 90 lights the light source 12 again. That is, for every image acquisition, this blinking operation is repeated.

Not limited to the above, the controller 90 may control the light source 12 to emit light multiple times (of course, including continuous emission) to obtain a plurality of endothelial images by the imaging device 44.

<Continuous Photographing Mode>

Hereinafter, in a continuous photographing mode, a description will be given of a process where endothelial cell images are continuously obtained at each fixation position using a plurality of fixation lamps.

FIG. 9 is a diagram illustrating an exemplary photographing screen displayed on the monitor 95. This diagram illustrates an anterior segment image. FIG. 10 is a diagram illustrating an exemplary fixation position setting screen. When the examiner operates a fixation light switch 96a on the monitor 95, the controller 90 displays the fixation position setting screen (hereinafter referred to as the setting screen) on the monitor 95. This screen displays respective fixation positions presented by the fixation optical systems. On this screen, corresponding to the respective fixation positions, a plurality of the buttons 310a to 310i and 320a to 320f are arranged. Pressing the buttons sets the fixation positions for continuous photographing. Here, the controller 90 may display the setting screen superimposed on the photographing screen.

The setting screen on the monitor 95 is roughly divided into a first corneal region 310 (310a to 310i) corresponding to the corneal center and the proximity of the corneal center and a second corneal region 320 (320a to 320f) corresponding to corneal peripheral region. In the first corneal region 310, fixation lamps (the visible light sources 71a to 71i) presented by the internal fixation optical system 70 are selectable. In the second corneal region 320, fixation lamps (the visible light sources 76a to 76f) presented by the external fixation optical system 75 are selectable.

The controller 90 determines the number of endothelium photographing and an illumination order of the fixation lamps based on an operation signal from the monitor (the touchscreen) 95 in the setting screen. The controller 90 displays a photographing order on the setting screen. The controller 90 stores the set fixation lamps and illumination order in the memory 92, and retains setting after the apparatus 100 is turned off.

More specifically, the controller 90 set the photographing order to an order of buttons pressed by the examiner. Every pressing of the button by the examiner, the controller 90 displays a display (such as a number or a graphic) of the photographing order above the pressed button or near the pressed button. The controller 90 performs selection display (such as check) indicating selection as a fixation position on the display of the selected switch. FIG. 10 is an example where nine fixation positions near the center including the corneal center are selected on the fixation position setting screen on the monitor 95. As above, the illumination positions and the illumination order of the fixation lamps are set. Subsequently, when the examiner presses an OK button on the screen, the controller 90 erases the fixation position setting screen and returns to the photographing screen as illustrated in FIG. 9.

The controller 90 displays a fixation position display 500 for displaying the fixation positions, which are set on the setting screen, on the monitor 95. The fixation position display 500 includes, for example, a current position display 510, a setting position display 520, and a non-setting position display 530. The current position display 510 indicates the position of the fixation lamp currently lighting. The setting position display 520 indicates the position of the fixation lamp preliminarily set on the setting screen. The non-setting position display 530 indicates the fixation position that is not selected on the setting screen.

Figure 12:
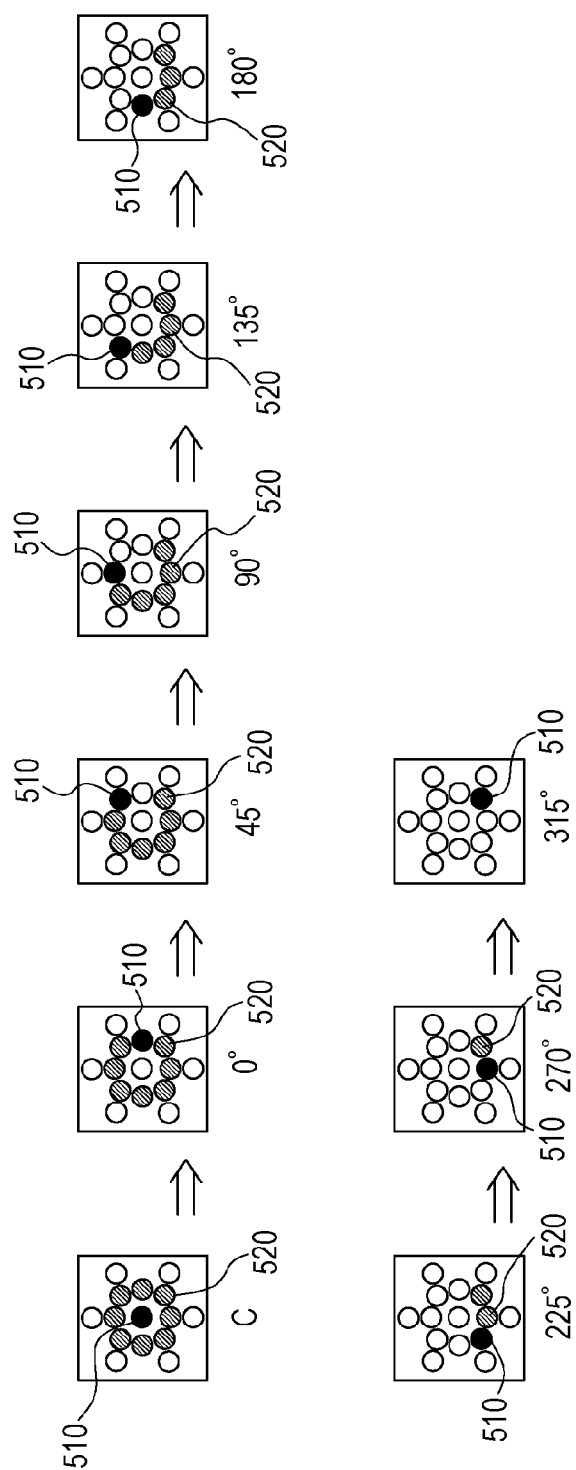
FIG. 12 is a diagram illustrating an exemplary sequence of fixation positions displayed on the monitor at respective fixation positions.

The controller 90 displays, for example, the fixation lamp currently lighting in a first color (such as green) as the current position display 510. The controller 90 displays, for example, the set fixation lamp in a second color (such as red) that is different from the first color as the setting position display 520. The controller 90 eliminates the color of the fixation lamp where the photographing has been terminated. This allows the examiner to visually obtain the current photographing position and the remaining photographing position. FIG. 12 is a diagram illustrating an example of the fixation position display 500 at each fixation position.

The controller 90 uses the illumination positions and the illumination order of the fixation lamps, which are set as described above, to control the fixation optical systems (the internal fixation optical system 70a to 70i and the external fixation optical system 75a to 75f) so as to sequentially change the fixation position for the examinee's eye. At each fixation position, the controller 90 controls the illumination optical system 10 and the imaging optical system 30 to sequentially obtain an endothelial cell images at a plurality of positions on the cornea.

A description will be given of, as an example, a case where nine fixation positions near the center including the corneal center are selected in the fixation position setting screen on the monitor 95 in an order illustrated in FIG. 10. After the transition to the photographing screen, the controller 90 lights the first selected fixation lamp (visible light source 71a) to guide the fixation direction of the eye E to the front direction. The examiner asks the examinee to gaze the fixation target.

The examiner performs alignment of the photographing unit 4 with respect to the eye E while observing the anterior segment image displayed on the monitor 95.

When the rough alignment is performed for the photographing unit 4 with respect to the eye E, the controller 90 detects the alignment state of the photographing unit 4 with respect to the eye E in the X- and Y-directions based on the imaging signal from the imaging device 64. Subsequently, the controller 90 controls the driving unit 6 based on the detection result. That is, the controller 90 moves the photographing unit 4 with respect to the eye E in the X- and Y-directions such that the alignment state to be detected in the X- and Y-directions satisfies the predetermined alignment allowable range.

The controller 90 detects the alignment state of the photographing unit 4 with respect to the eye E in the Z direction based on the light reception result of the light receiving device 89. Subsequently, the controller 90 controls the driving unit 6 based on the detection result. That is, the controller 90 moves the photographing unit 4 in the Z direction such that the alignment state to be detected in the Z direction satisfies the predetermined allowable range.

In the case where the alignment state in the XYZ directions satisfies the alignment completion condition by the above-described alignment operation, the controller 90 determines that the alignment in the XYZ directions is completed properly.

When it is determined that the alignment is completed properly, the controller 90 controls the driving of the driving unit 6 to move the photographing unit 4 in a predetermined direction. Subsequently, the controller 90 allows the illumination light source 12 to continuously emit light during the movement of the photographing unit 4. Simultaneously, the controller 90 allows the imaging device 44 to obtain a plurality of endothelial images. The obtained endothelial images are stored in the memory 92.

Figure 11:
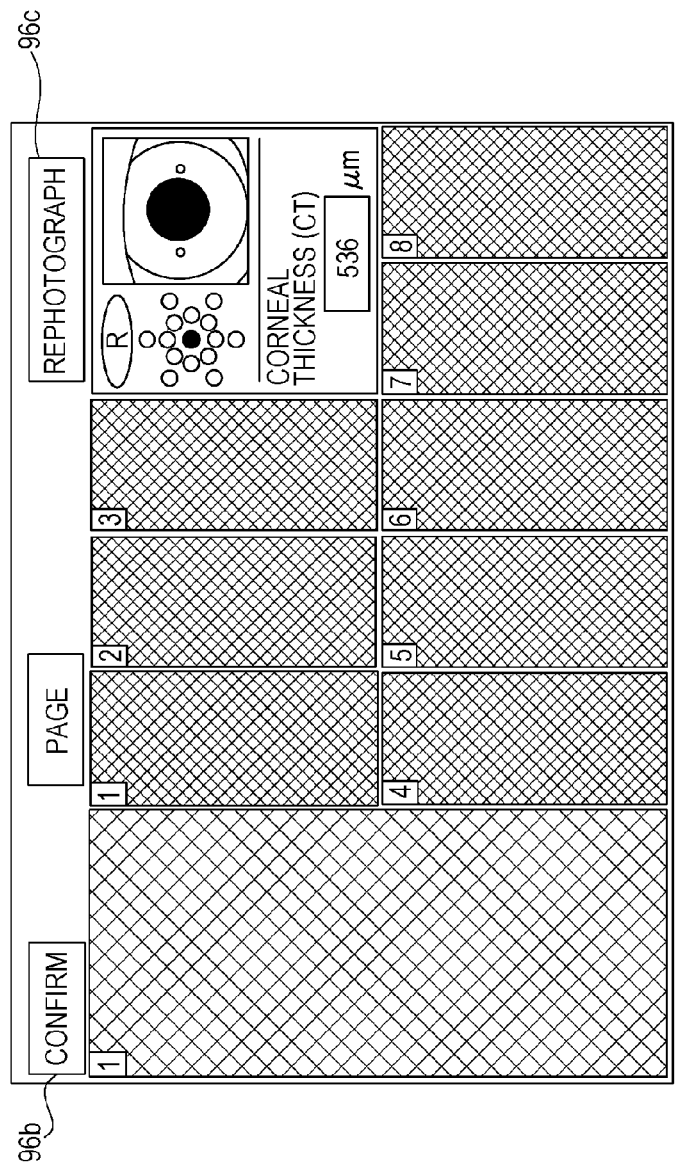
FIG. 11 is a diagram illustrating an exemplary confirmation screen of the photographing screen on the monitor.

FIG. 11 is a diagram illustrating an exemplary confirmation screen for photographed images. When an endothelial image is obtained at the first fixation position, the controller 90 terminates the photographing operation. On the monitor 95, the screen transitions to the confirmation screen for photographed images. Pressing a confirmation button 96b allows the controller 90 to analyze the selected image. While the confirmation screen is displayed on the monitor 95, the controller 90 inhibits photographing of the endothelial image. In this embodiment, the confirmation screen for the photographed images double as a selection screen for analyzing an image among a plurality of endothelial images. Therefore, when an endothelial image desired by the examiner is selected on the touchscreen (the monitor 95) and the confirmation button 96b is pressed on the confirmation screen, the controller 90 analyzes the selected image.

When the analysis of the selected image is terminated, the controller 90 makes the transition from the confirmation screen for the photographed images to the photographing screen. The controller 90 returns to the photographing screen, and simultaneously switches the fixation lamp to be lighted from the center position to the next fixation position (71b).

On the other hand, pressing a re-photographing button 96c allows the controller 90 to switch the screen on the monitor 95 from the confirmation screen for the photographed images to the photographing screen. At this time, the controller 90 does not switch the illuminated position of the fixation lamp, and performs re-photographing in the first fixation position while the first fixation lamp (visible light source 71a) is maintained. When the re-photographing is completed, the controller 90 allows the transition to the confirmation screen again.

The controller 90 can control the driving unit 6 based on the signals from the imaging device 64 and the light receiving device 89 also in the display of the confirmation screen for the photographed images. For example, the controller 90 may control the photographing unit 4 to track the eye E (tracking control). On the confirmation screen, when the eye E deviates from the alignment allowable range, the controller 90 controls the driving unit 6 to return to the alignment allowable range. This maintains a relative position between the eye E and the photographing unit 4 at a proper position to prepare for the next photographing.

After the transition to the photographing screen, the controller 90 permits photographing of the endothelial image subject to completion of the alignment. The controller 90 continues the tracking control of the photographing unit 4 with respect to the eye E. When it is determined that the alignment is completed properly, the controller 90 controls the driving of the driving unit 6 to move the photographing unit 4 in a predetermined direction. The controller 90 allows the illumination light source 12 to continuously emit light during the movement of the photographing unit 4, and simultaneously allows the photographing unit 4 to obtain a plurality of endothelial images. The controller 90 stores the obtained endothelial images in the memory 92.

As described above, when an endothelial image is obtained at the next fixation position, the controller 90 switches the screen of the monitor 95 to the confirmation screen for the photographed images similarly to the case where the first endothelial image is obtained. Pressing the confirmation button 96b by the examiner allows the controller 90 to start analyzing the photographed image. When the analysis is completed, the controller 90 switches the monitor 95 from the confirmation screen to the photographing screen. The controller 90 returns to the photographing screen, and simultaneously switches the fixation lamp to be lighted from the center position to the next fixation position (in a 45° position).

On the other hand, pressing the re-photographing button 96c by the examiner allows the controller 90 to switch the screen of the monitor 95 from the confirmation screen for the photographed images to the photographing screen. In this case, the controller 90 does not switch the illuminated position of the fixation lamp. The controller 90 allows the photographing unit 4 to perform re-photographing at the second fixation position while the second fixation lamp (visible light source 71b) is maintained. When the re-photographing is completed, the controller 90 switches the screen on the monitor 95 to the confirmation screen again.

As described above, the controller 90 sequentially changes the fixation position (from the center, 0°, 45°, . . . and 315° in this order) to obtain a plurality of preliminarily set endothelial images. At each fixation position, the controller 90 allows the photographing unit 4 to obtain the endothelial image, and stores the obtained endothelial image in the memory 92. When all the photographing assignments are completed at the set fixation positions, the controller 90 lights the fixation lamp corresponding to the first fixation position (the center).

As described above, the controller 90 lights the fixation lamp corresponding to the next fixation position, and simultaneously allows the illumination light source 12 to emit light in a proper alignment condition of the photographing unit 4 with respect to the eye E. Also, the controller 90 allows transition of the photographing unit 4 to a photographing permission state where the endothelial image can be photographed to smoothly obtain the endothelial image at the next fixation position.

In the above description, the controller 90 continues auto tracking operation in the step for displaying the confirmation screen for the endothelial image on the monitor 95. Accordingly, in a previous step for switching the fixation position, positioning of the photographing unit 4 with respect to the examinee's eye is almost completed in advance. After the screen of the monitor 95 is switched to the photographing screen, the controller 90 allows switching to the next fixation position and simultaneously transition of the photographing unit 4 to the state where the photographing by the auto shot is possible so as to more smoothly obtain the endothelial image at the next position.

While in the above-described configuration the fixation position display 500 indicates the information related to the photographing position, this should not be construed in a limiting sense. Any configuration is possible insofar as the controller 90 display the photographing position display for determining the current photographing position, the plurality of preliminarily set photographing positions, and non-set photographing positions on the monitor 95. For example, the controller 90 may use a graphic display that displays a graphic schematically indicating the anterior segment on the monitor 95 and further expresses the photographing position on the anterior segment.

Switching of Fixation Positions Based on Determination Results of Photographed Images Hereinafter, a description will be given of an example in the case where the fixation positions are switched based on determination results of the photographed images. The controller 90 determines whether or not image quality of the obtained endothelial image is within a predetermined range by image processing. In the case where the image quality of the endothelial image is determined to be within the predetermined range, the controller 90 controls the fixation optical systems 70 and 75 and switches the illuminated position of the fixation lamp to obtain an endothelial image at the next fixation position. On the other hand, in the case where the image quality of the endothelial image is determined not to be within the predetermined range, the controller 90 does not switch the illuminated position of the fixation lamp and obtains the endothelial image again. The controller 90 uses, for example, a sum of luminance values in the endothelial image and the number of edges in the endothelial image as evaluation values for evaluating the image quality of the endothelial image. The controller 90 determines whether or not the evaluation value is within the predetermined range.

Next, a description will be given of a case where a plurality of endothelial images is obtained for each fixation position. Regarding the respective endothelial images obtained after obtaining the endothelial image at the first fixation position, the controller 90 calculates evaluation values of the plurality of obtained endothelial images. The controller 90 determines an endothelial image with the highest evaluation value. Regarding this endothelial image, the controller 90 determines whether or not the evaluation value is within the predetermined range. The controller 90 displays the evaluation value on the monitor 95.

In the case where the evaluation value of the endothelial image with the highest evaluation value is equal to or more than a predetermined threshold value, the controller 90 switches the fixation lamp to be lighted from the first fixation position to the next fixation position (the second fixation position). The controller 90 permits photographing of the endothelial image subject to completion of the alignment for the photographing unit 4 with respect to the eye E. The controller 90 continues tracking control of the photographing unit 4 with respect to the eye E. In the case where the alignment is determined to be proper, the controller 90 controls the driving of the driving unit 6 to move the photographing unit 4 in a predetermined direction. The controller 90 allows the illumination light source 12 to continuously emit light during the movement of the photographing unit 4, and simultaneously allows the imaging device 44 to obtain a plurality of endothelial images. The controller 90 stores the obtained endothelial images in the memory 92. Subsequently, after obtaining the endothelial images at the second fixation position, the controller 90 calculates respective evaluation values of the plurality of the obtained endothelial images. Regarding the endothelial image with the highest evaluation value, the controller 90 determines whether or not the evaluation value is within a predetermined range. By repeating this operation, the controller 90 obtains the endothelial images at three or more fixation positions.

In the case where the evaluation value is lower than the threshold value, the controller 90 does not switch the illuminated position of the fixation lamp. That is, the controller 90 allows the imaging device 44 to perform re-photographing at the first fixation position while the first fixation position is maintained. Subsequently, regarding the endothelial image with the highest evaluation value, the controller 90 determines whether or not the evaluation value is within the predetermined range. This allows smoothly obtaining the image even when a photographing error occurs. Here, the controller 90 may be configured to select whether or not automatic re-photographing is performed.

The controller 90 may notify the examinee about a change in position of the fixation lamp (for example, controls an audio unit to generate a beep sound) when the fixation lamp moves. Based on the operation signal from the examiner, a mode for switching the fixation position and a mode for switching the fixation position based on a propriety determination result of the endothelial image may be selected. The configuration may allow the examiner to select the threshold value for switching to the next fixation position.

In the photographing screen on the monitor 95 illustrated in FIG. 9, a photographing result button 400 is used as a switch for transitioning from the photographing screen to a screen for displaying the result of photographing an endothelial image. When the photographing result button 400 is pressed, the control unit 90 ends the photographing and displays the photographing result screen (see FIGS. 13A and 13B) on the monitor 95.

Figure 13B:
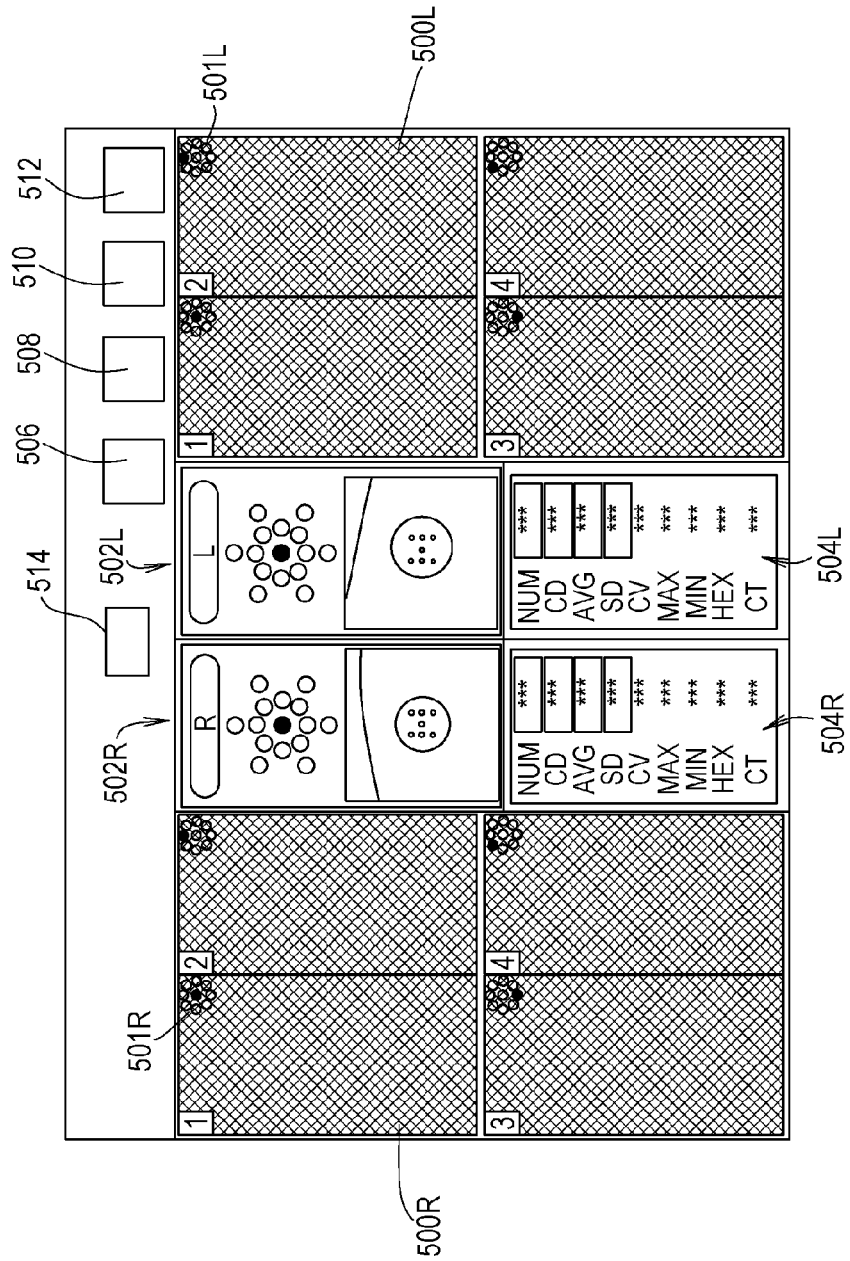
FIG. 13B is a diagram illustrating an example of a photographing result screen (multiple display) according to the present embodiment.

FIGS. 13A and 13B are diagrams each illustrating an example of the photographing result screen. According to the present embodiment, two types of the photographing result screen are prepared. One is single display (see FIG. 13A) for showing the result of photographing the left and right eyes each once, and the other is multiple display (see FIG. 13B) for showing the result of photographing the left and right eyes each a plurality of times.

<Single Display>

As illustrated in FIG. 13A, the single display screen displays the following: a right eye endothelial image 500R; a left eye endothelial image 500L; a photographed eye display 502R showing the photographed eye (right eye); a photographed eye display 502L showing the photographed eye (left eye); an analysis value 504R indicating the result of analysis of an obtained right eye endothelial image; an analysis value 504L indicating the result of analysis of an obtained left eye endothelial image; a delete button 506 for deleting photographing data; a print button 508 for printing the displayed endothelial images and analysis results; and a photographing button 509 for switching the screen on the monitor 95 to the photographing screen.

In the single display screen illustrated in FIG. 13A, the control unit 90 divides the screen of the monitor 95 into a plurality of regions, namely, a central region and regions on both left and right sides of the central region.

The central region is divided into left and right parts. One of the parts is provided for displaying the fixation position information and analysis result for the left eye, and the other is provided for displaying the fixation position information and analysis result for the right eye. Namely, the photographed eye displays 502R and 502L and the analysis values 504R and 504L are displayed in the central region. The regions on both the left and right sides of the central region are regions for displaying respective endothelial images. Specifically, in one region, the left eye endothelial image 500L is displayed, while in the other region the right eye endothelial image 500R is displayed.

In the single display screen illustrated in FIG. 13A, the endothelial images 500R and 500L are endothelial images of the left and right eyes for analysis that have been selected in an image selection screen. As illustrated, the endothelial images 500R and 500L are displayed so as to sandwich the left and right photographed eye displays 502R and 502L.

In the photographed eye displays 502R and 502L, photographed eye information (left and right eyes, and sight fixation light illuminated positions) of the displayed endothelial images are displayed. The photographed eye displays 502R and 502L are displayed adjacent to each other. In the analysis values 504R and 504L, the analysis results for the displayed endothelial images are displayed.

The analysis result includes the number of cells NUM, endothelial cell density CD, an average endothelial area AVG, a standard deviation SD, a coefficient of variation CV, a maximum area MAX, a minimum area MIN, and a hexagonal cell appearance ratio HEX. Further, in the columns for the analysis values 504R and 504L, a corneal thickness CT that is measured simultaneously with the endothelial image is displayed.

When the delete button 506 is pressed, the photographing data are deleted from the screen of the monitor 95. After the deletion, the screen of the monitor 95 is automatically switched from the single display screen to an observation screen. When the print button 508 is pressed, the displayed endothelial images and analysis values are printed by a built-in printer (not shown). When the photographing button 509 is pressed, the screen of the monitor 95 is switched to the observation screen, and photographing is newly started.

The single display has the following advantages: The examiner can easily confirm the result of photographing the left and right eyes each once. Thus, the single display is useful for quickly confirming the state of the endothelium of the left and right eyes. Here, the sight fixation light display corresponding to each endothelial image is allocated in the single display screen, so that the examiner can easily grasp the photographed site of the endothelium. Further, the examiner can grasp the appropriateness of photography as the anterior segment image corresponding to the displayed endothelial image is displayed on the monitor 95. Further, the examiner can easily grasp the analysis result based on the displayed endothelial image because the analysis values are displayed on the monitor 95.

<Multiple Display>

As in the case of the single display screen, as illustrated in FIG. 13B, the multiple display screen displays the following: the right eye endothelial image 500R; the left eye endothelial image 500L; the photographed eye display 502R showing the photographed eye (right eye); the photographed eye display 502L showing the photographed eye (left eye); the analysis value 504R indicating the result of analysis of the obtained right eye endothelial image; the analysis value 504L indicating the result of analysis of the obtained left eye endothelial image; the delete button 506 for deleting photographing data; the print button 508 for printing the displayed endothelial images and analysis results; and the photographing button 509 for switching the screen on the monitor 95 to the photographing screen. Further, in the multiple display screen, a page button 512 and an integrated display button 514 are displayed. The page button 512 and the integrated display button 514 will be described later.

In the multiple display, a plurality of endothelial images is displayed for each of the left and right eyes, and data for displaying the analysis value are selected. Unless otherwise specifically stated, the apparatus configuration used for the multiple display is the same as the apparatus configuration for the single display.

In the multiple display screen illustrated in FIG. 13B, the control unit 90 divides the screen of the monitor 95 into a plurality of regions, namely, a central region and regions positioned on both left and right sides of the central region. The central region is divided into left and right parts. One of the parts is provided for displaying fixation position information and analysis result for the left eye, and the other is provided for displaying fixation position information and analysis result for the right eye.

The central region is divided into the left and right parts. One of the parts is provided for displaying fixation position information and analysis result for the left eye, and the other is provided for displaying fixation position information and analysis result for the right eye. Namely, in the central region, the photographed eye displays 502R and 502L and the analysis values 504R and 504L are displayed. The regions positioned on both left and right sides of the central region are regions for displaying the respective endothelial images. Specifically, in one region, a plurality of the left eye endothelial images 500L is displayed, and in the other region, a plurality of the right eye endothelial images 500R is displayed.

In the endothelial images 500L and 500R, the corresponding sight fixation light displays (fixation position displays) 501R and 501L are respectively displayed. The number of endothelial images of each eye to be displayed on one screen is determined in advance (such as 4). When the predetermined number of the endothelial images of each eye (such as 4) is exceeded, the examiner can press the page button 512 to switch the displayed endothelial images to the next endothelial image.

In the multiple display screen, the control unit 90 updates the photographed eye displays 502R and 502L and the analysis values 504R and 504L depending on the selected endothelial images, respectively. Here, one image, for which the photographed eye display and the analysis value are displayed, is selected from the endothelial images on each of the left and right sides. Thus, in the photographed eye displays 502R and 502L and the analysis values 504R and 504L on the screen of the monitor 95, data corresponding to the selected endothelial images are displayed. The control unit 90 highlights the selected images such that the selected images can be distinguished from the other images (such as by using a colored figure number or a frame surrounding the image).

The multiple display has the following advantages: The examiner can easily grasp the result of photographing the left and right eyes each a plurality of times. Thus, the multiple display is useful for quickly confirming the state of endothelium of the left and right eyes. Here, the sight fixation light display is allocated to each of the plurality of endothelial images on the multiple display screen, so that the examiner can easily grasp the photographed site corresponding to the plurality of endothelial images. Further, the examiner can grasp the photographic appropriateness of the selected endothelial images as the anterior segment images corresponding to the selected endothelial image are displayed on the monitor 95. The examiner can easily grasp the analysis results based on the selected endothelial images as the analysis values corresponding to the selected endothelial images are displayed on the monitor 95.

The single display or multiple display of the photographing result is determined by mode selection between a single mode and a multiple mode in a predetermined parameter setting screen (not shown).

When the single mode is selected, the control unit 90 displays the photographing result screen in the single display (see FIG. 13A) regardless of the number of times of photographing. Upon completion of photographing of the left and right eyes each once, the completion acts as a trigger to cause the control unit 90 to switch the screen of the monitor 95 from the photographing screen to the photographing result screen, using the completion as a trigger. Thus, the examiner can easily confirm the photographing results for the left and right eyes. In the single mode, the number of times of photographing is one for each of the left and right. When the number is exceeded, the previous image data are erased from the screen of the monitor 95 and only the latest photographing data are displayed.

When the multiple mode is selected, the control unit 90 switches the display between the single display (FIG. 13A) and the multiple display (FIG. 13B) depending on the number of times of photographing. In the multiple mode, in the case that the photographing is performed up to once for each of the left and right eyes, the photographing result screen is displayed on the monitor 95 in the single display when the photographing result button 400 is pressed. On the other hand, in the case that the photographing is performed more than once for each of the left and right eyes, the photographing result screen is displayed on the monitor 95 in the multiple display when the photographing result button 400 is pressed. Thus, the photographing result display screen is changed according to the number of times of photographing, so that the examiner can easily confirm the photographing result.

In the multiple mode, image data up to a predetermined number of times (such as 10) for each of the left and right are stored in the memory 92. When the number of times of photographing exceeds the upper limit, the image data are deleted from the memory 92 in chronological order. In the single mode, the number of times of photographing is once for each of the left and right, and the previous image data are erased from the memory 92 when the photographing is repeated.

<Integrated Display>

In the multiple display screen (see FIG. 13B), when the integrated display button 514 is pressed, the screen of the monitor 95 is changed to the integrated display screen (see FIG. 14). In the integrated display screen, an integrated image display region 610, an analysis result display region 630, and a magnified image display region 640 are displayed. In the integrated display screen, endothelial images and analysis results (data) regarding one of the left and right eyes are output. The output of the data for one eye can be switched to the output of the data for the other eye by a left/right eye switch button 650.

<Integrated Image Display Region>

In the integrated image display region 610, a first endothelial image 610a of the corneal central portion is displayed. A plurality of second endothelial images 610b to 610i photographed at different positions from the corneal central portion is arranged with reference to the first endothelial image 610a. The second endothelial images 610b to 610i are, for example, second endothelial images photographed at a plurality of positions in an adjacent region to the corneal central portion. The first endothelial image 610a and the second endothelial images 610b to 610i are spaced apart from each other when displayed on the monitor 95, as illustrated in FIG. 14. Such an arrangement of images is adopted so that the examiner can easily grasp the state of cells in each endothelial image. FIG. 15 is a diagram illustrating an example of the positional relationship between a corneal central portion CE, an adjacent region PAR to the corneal central portion, and a cornea peripheral region PER on the cornea. In this figure, hatched portions correspond to the photographed regions, respectively.

The first endothelial image 610a and the second endothelial images 610b to 610i are displayed side by side corresponding to, for example, the fixation positions of the fixation optical system. At the center of the images, for example, the first endothelial image 610a is arranged. The second endothelial images 610b to 610i are arranged corresponding to the fixation positions with respect to the corneal central portion. For example, in the case of the endothelial image 610c obtained with the visible light source 71c (sight fixation light), because the visible light source 71c is positioned above the visible light source 71a used as the central sight fixation light, the endothelial image 610c is displayed above the first endothelial image 601a. The other endothelial images are also arranged according to the positions of the sight fixation lights with respect to the central sight fixation light.

Position displays 620a to 620i indicating their corresponding positions on the cornea of the examinee's eye are respectively allocated to the first endothelial image 610a and the second endothelial images 610b to 610i. The position displays 620a to 620i are provided, for example, for indicating the fixation positions at the time when the endothelial images were photographed. The position displays 620a to 620i may be symbol displays illustrated in FIG. 14. Alternatively, the fixation positions may be respectively indicated by the letters of the alphabet. The position displays 620a to 620i may be overlapped with the respective endothelial images, as illustrated in FIG. 14, or they may be displayed adjacent to the corresponding endothelial images.

The endothelial images displayed in the integrated image display region 610 are set on the basis of the photographing position on the cornea. Namely, according to the present embodiment, a setting is made such that the photographed endothelial images are output in the integrated image display region 610 at the corneal central portion position and at a plurality of photographed positions at regular intervals (of a predetermined angle such as) 45° on a circumference about the corneal central portion. According to the present embodiment, the photographing positions on the cornea are indirectly identified on the basis of the fixation positions of the fixation optical system. When an endothelial image corresponding to a set photographing position is not obtained, the display region for that endothelial image is left blank.

<Analysis Result Display Region>

The analysis result for the endothelial images displayed on the monitor 95 is displayed in the analysis result display region 630. For example, the analysis result includes, as illustrated in FIG. 14, the number of cells NUM, the endothelial cell density CD, the coefficient of variation CV, and the hexagonal cell appearance ratio HEX. However, the analysis result is not limited to the above, and may include parameters used for corneal endothelial analysis. Examples of the parameters include the number of cells NUM, the endothelial cell density CD, the average endothelial area AVG, the standard deviation SD, the coefficient of variation CV, the maximum area MAX, the minimum area MIN, and the hexagonal cell appearance ratio HEX.

More specifically, the parameters are as follows: The number of cells NUM is the number of analyzed endothelial cells. The endothelial cell density CD is the number of endothelial cells per unit area. The average endothelial area AVG is an average area of the analyzed endothelial cell areas. The standard deviation SD is the standard deviation of the analyzed endothelial cell areas. The coefficient of variation CV is a value obtained by dividing the standard deviation SD by the average endothelial area AVG. The maximum area MAX is the largest area of the analyzed endothelial cells. The minimum area MIN is the smallest area of the analyzed endothelial cells. The hexagonal cell appearance ratio HEX indicates the ratio of cells having hexagonal cell characteristics to the analyzed endothelial cells.

The control unit 90 may determine the above parameters by processing an endothelial image stored in the memory 92 according to a predetermined algorithm. For example, the control unit 90 extracts the individual endothelial cells from the endothelial image by image processing based on a brightness distribution in the endothelial image, and calculates the parameters based on the number, area, and the like of the extracted endothelial cells. A well-known technique may be employed as a technique for determining the parameters by processing the endothelial image, and therefore a detailed description of the technique will be omitted. During the calculation of the parameters, a part of the image processing by the control unit 90 may be supplemented by manual operation by the examiner.

The control unit 90 displays, for example, an analysis result 630a for a selected endothelial image and an analysis result 630b for the plurality of endothelial images displayed on the monitor in the analysis result display region 630.

The control unit 90 displays the analysis result for an endothelial image selected from the plurality of endothelial images displayed on the monitor 95. For example, the examiner touches at least one of the plurality of endothelial images. The control unit 90 displays the analysis result for the endothelial image selected by the touch input on the monitor 95. The control unit 90 also displays a magnified image 640Z of the selected endothelial image in the magnified image display region 640.

In this way, the examiner can easily confirm the magnified image 640Z of the endothelial image of interest to the examiner and the analysis result therefor. The examiner can further compare the magnified image and its analysis result with the magnified image and its analysis result for an endothelial image obtained at another position. When the magnified image 640Z of the selected endothelial image is displayed, the magnified image may be displayed in a window separate from the window for the integrated display screen.

An integrated analysis result regarding the plurality of endothelial images displayed on the monitor 95 is displayed in the analysis result display region 630. For example, the integrated analysis result includes the number of cells NUM, the endothelial cell density CD, the coefficient of variation CV, and the hexagonal cell appearance ratio HEX, as illustrated in FIG. 14. The integrated analysis may be an analysis result based on at least two endothelial images displayed on the monitor 95. For example, as illustrated in FIG. 14, an analysis result based on all of the endothelial images 610a to 610i (except for the magnified image 640Z) displayed on the monitor 95 is output. An analysis result based on the endothelial images 610b to 610i adjacent to the corneal central portion may be output in the analysis result display region 630. The positions of the endothelial images 610b to 610i adjacent to the corneal central portion may be classified with reference to the corneal central portion. For example, an analysis result based on a plurality of endothelial images 610c to 610e positioned higher than the corneal central portion may be output in the analysis result display region 630 on the screen of the monitor 95.

In the following, an example will be described in which the analysis result based on all of the endothelial images 610a to 610i (excluding the magnified image 640Z) displayed on the monitor 95 is output in the analysis result display region 630 on the screen of the monitor 95.

In the integrated analysis, the number of cells NUM is determined by adding up the result of the number of cells analyzed in each of the endothelial images 610a to 610i. The integrated analysis result of the endothelial cell density CD, the coefficient of variation CV, and the hexagonal cell appearance ratio HEX is obtained by averaging the analysis results for the endothelial images 610a to 610i. On the basis of the integrated analysis result of the maximum area MAX and the minimum area MIN, relevant cells (cells having the maximum area and cells having the minimum area) are identified from the endothelial images 610a to 610i, and the area of the identified cells is displayed in the analysis result display region 630. When the integrated analysis result is obtained, the technique is not limited to the above that determines the integrated analysis result from the values of the analysis results. The control unit 90 may extract the endothelial cells by subjecting the plurality of endothelial images to image processing all at once, and calculate the parameters based on the number and area and the like of the extracted endothelial cells.

Because the integrated analysis result for a plurality of endothelial images is output on an output apparatus (such as the monitor) as described above, the number of cells that are detected can be increased, whereby the reliability of analysis in the corneal central portion and an adjacent region can be increased.

Thus, the integrated analysis has the following advantages. When an analysis is conducted on an eye in which the endothelium is difficult to observe, such as a diseased eye (such as corneal endotheliitis and corneal guttata), the number of detected cells may be decreased greatly. Thus, as described above, by integrating the analysis results for the respective endothelial images, the number of detections can be greatly increased even with a diseased eye, so that the reliability of analysis can be increased.

In the foregoing description, the endothelial images 610a to 610i are spaced apart from each other in the single screen of the monitor 95. However, they are not limited thereto. The control unit 90 may dispose the endothelial images 610a to 610i such that, in consideration of their photographing positions on the actual cornea, the images are displayed overlapping with each other where the actual photographing areas are overlapping with each other. A configuration may also be adopted such that the examiner can select a layout for the integrated display of the endothelial images 610a to 610i as desired.

In the foregoing description, the arrangement of the endothelial images 610a to 610i is such that the display positions of the endothelial images 610a to 610i in the integrated display is associated with the illuminated positions of the sight fixation lights. However, the arrangement of the endothelial images 610a to 610i is not limited to the above. For example, the control unit 90 may arrange the endothelial images 610a to 610i in association with the photographing positions on the cornea with respect to the corneal central portion. In this case, the display position of each endothelial image is determined with reference to the corneal central portion. For example, an endothelial image obtained above the corneal central portion is displayed above the endothelial image 610a. In this display system, the examiner can intuitively grasp the positional relationship of an adjacent endothelial image to the corneal central portion from the arranged position of the endothelial image. Thus, the examiner can easily identify the diseased site and easily grasp its position.

Figure 16A:
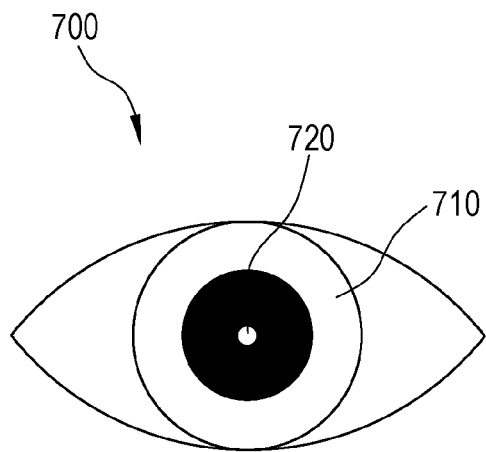
FIG. 16A is a diagram illustrating an example of a symbol display according to the present embodiment.
Figure 16B:
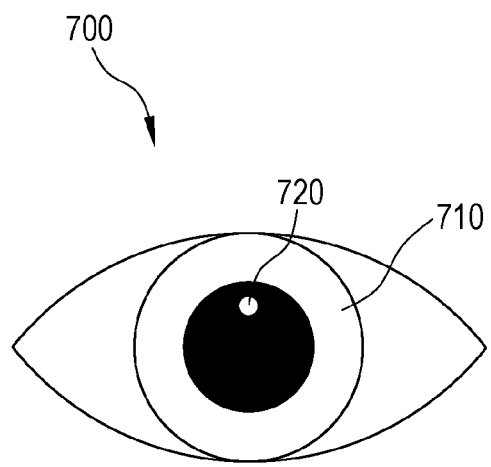
FIG. 16B is a diagram illustrating an example of the symbol display according to the present embodiment, as in FIG. 16A.

In the foregoing description, the position displays 620a to 620i allocated to the endothelial images 610a to 610i are displays indicating the fixation positions. However, they are not limited thereto. It is merely required that the position information about the obtained endothelial image can be confirmed. For example, the position displays 620a to 620i allocated to the endothelial images 610a to 610i may be displays indicating the photographing positions on the cornea, such as the symbol display 700 illustrated in FIGS. 16A and 16B. The symbol display 700 illustrated in FIGS. 16A and 16B includes a first graphic image 710 indicating the cornea of the examinee's eye, and a second graphic image 720 indicating the photographing position on the cornea (the first graphic image) 710. In FIG. 16A, the second graphic image 720 is positioned at the center of the first graphic image 710. In FIG. 16B, the second graphic image 720 is at a position displaced (above) from the center of the first graphic image 710. Such a graphic display enables the examiner to easily recognize the photographing position of the endothelial image. Of course, it is not limited to the symbol display, and the photographing position on the cornea may be indicated by the letters of the alphabet or the like.

In the foregoing description, in the integrated image display region 610, the endothelial image at the corneal central portion and the endothelial images adjacent to the corneal central portion are simultaneously displayed. However, this is not to be taken as limiting the display of images in the integrated image display region 610. For example, a plurality of endothelial images photographed at different positions on the cornea may be simultaneously displayed in the integrated image display region 610. Further, correspondingly to the endothelial image displayed on the monitor 95, the analysis result is output in the analysis result display region 630 on the screen of the monitor 95.

For example, the control unit 90 may display a plurality of endothelial images photographed at different positions adjacent to the corneal central portion simultaneously in the integrated image display region 610. The control unit 90 may also display the endothelial image at the corneal central portion and a plurality of endothelial images photographed at different positions adjacent to the cornea simultaneously in the integrated image display region 610. The control unit 90 may also display the endothelial image at the corneal central portion, a plurality of endothelial images photographed at different positions adjacent to the corneal central portion, and a plurality of endothelial images photographed at different positions at the periphery of the cornea simultaneously in the integrated image display region 610. Namely, the endothelial images displayed in the integrated image display region 610 may include an appropriate combination of an endothelial image at the corneal central portion, an endothelial image adjacent to the corneal central portion, and an endothelial image at the periphery of the cornea.

When displaying a plurality of endothelial images at and adjacent to the corneal central portion and a plurality of endothelial images at the periphery of the cornea simultaneously in the integrated image display region 610, the control unit 90 may display an integrated analysis result based on the plurality of endothelial images at and adjacent to the corneal central portion, and an integrated analysis result based on the plurality of endothelial images at the periphery of the cornea in the analysis result display region 630.

Figure 17:
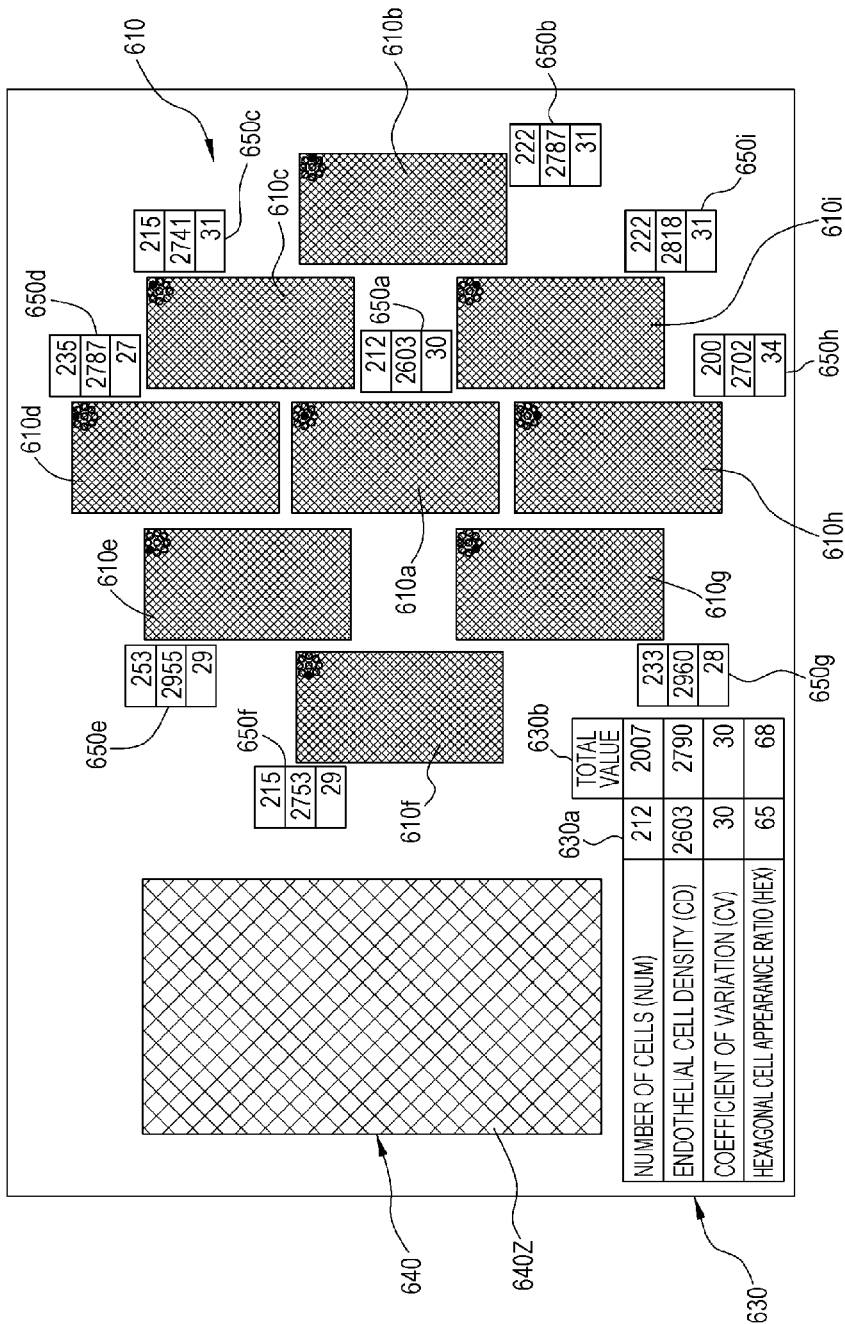
FIG. 17 is a diagram illustrating a display example of analysis results for individual endothelial cell images.

The control unit 90 may display the analysis result for each of the endothelial cell images displayed on the monitor 95 in the analysis result display region 630 (see FIG. 17). For example, the control unit 90 may display analysis results 650a to 650i regarding the endothelial images 610a to 610i in the analysis result display region 630. The control unit 90 may display the analysis results 650a to 650i in proximity to the display regions for the endothelial images 610a to 610i.

The present disclosure is not limited to the embodiments described above and may include various modifications. The present disclosure includes the modifications within the scope of the same technical idea. Further, such modifications may be made by persons with ordinary skills in the art within the technical idea of the present disclosure.

The corneal endothelial cell photographing apparatus according to the present embodiment may be any of the following first to ninth corneal endothelial cell photographing apparatuses.

The first corneal endothelial cell photographing apparatus is a corneal endothelial cell photographing apparatus for photographing an endothelial cell in the cornea of the examinee's eye, including:

an optical system for photographing an endothelial cell image of the examinee's eye, the optical system including an illuminating optical system for irradiating the cornea of the examinee's eye with illuminating light, and a light receiving optical system for receiving reflected light from the cornea including the corneal endothelial cell, the light receiving optical system including a light detector;

an image processor for obtaining an analysis result regarding the endothelial cell of the examinee's eye by processing the endothelial cell image, and for obtaining an integrated analysis result integrating the analysis results regarding a plurality of endothelial cell images photographed at different positions on the cornea of the examinee's eye; and a display controller that simultaneously displays the plurality of endothelial cell images on a monitor with reference to an endothelial cell image photographed at the corneal central portion, and that displays the integrated analysis result in the same screen.

The second corneal endothelial cell photographing apparatus is the first corneal endothelial cell photographing apparatus in which the display controller displays an endothelial cell image photographed at the corneal central portion and a plurality of endothelial cell images photographed at a plurality of positions in a region adjacent to the corneal central portion simultaneously on the monitor.

The third corneal endothelial cell photographing apparatus is the first corneal endothelial cell photographing apparatus which further includes an operating unit operated by an examiner, wherein the display controller displays at least one of the plurality of endothelial cell images on the monitor that is selected on the basis of an operation signal input from the operating unit in a magnified manner relative to the other endothelial cell images, the display controller also displaying an analysis result regarding the endothelial cell image displayed in a magnified manner.

The fourth corneal endothelial cell photographing apparatus is the first corneal endothelial cell photographing apparatus in which the display controller arranges the endothelial cell images displayed on the monitor apart from each other.

The fifth corneal endothelial cell photographing apparatus is the first corneal endothelial cell photographing apparatus which is provided with a photographing position changing unit for changing the endothelial cell photographing position on the cornea of the examinee's eye with respect to vertical and horizontal directions.

The sixth corneal endothelial cell photographing apparatus is the first corneal endothelial cell photographing apparatus which is provided with a fixation optical system including a plurality of sight fixation lights for changing the line of sight of the examinee's eye.

The seventh corneal endothelial cell photographing apparatus is the first corneal endothelial cell photographing apparatus which is provided with a drive unit for moving the illuminating optical system and the light receiving optical system in vertical and horizontal directions with respect to the examinee's eye.

The eighth corneal endothelial cell photographing apparatus is the first corneal endothelial cell photographing apparatus in which the display controller allocates a position display for indicating the position of each endothelial cell image to each endothelial cell image.

The ninth corneal endothelial cell photographing apparatus is the first corneal endothelial cell photographing apparatus in which the display controller further displays the analysis result for each of the endothelial cell images displayed on the monitor.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto

What is claimed is:

1. A corneal endothelial cell photographing apparatus for photographing an endothelial cell in the cornea of the examinee's eye, comprising:

an optical system;

an image processor; and a display controller, wherein the optical system includes an illuminating optical system for irradiating the cornea with illuminating light, and a light receiving optical system including a light detector and configured to receive reflected light from the cornea including the endothelial cell, the image processor analyzes each of a plurality of endothelial cell images photographed at different positions on the cornea, acquires an integrated analysis result by integrating the result of analysis of each of the plurality of endothelial cell images, and comprises data of the integrated analysis result comprising at least one selected from a group consisting of a sum of numbers of endothelial cells, an average value of endothelial cell densities, an average value of coefficients of variation, an average value of hexagonal cell appearance ratios, and a largest area of endothelial cells; the coefficient of variation being a product of a standard deviation of an endothelial cell area divided by an average endothelial area the sum of numbers of endothelial cells, the average value of endothelial cell densities, the average value of coefficients of variation, the average value of hexagonal cell appearance ratios, and the largest area of endothelial cells being a value obtained by analyzing at least two of the endothelial cell images photographed at different positions, and the display controller displays the plurality of endothelial cell images simultaneously on a monitor with reference to an endothelial cell image photographed at a central portion of the cornea, and displays the integrated analysis result on the same screen as for the plurality of endothelial cell images.

2. The corneal endothelial cell photographing apparatus according to claim 1, wherein the display controller displays the endothelial cell image photographed at the central portion of the cornea and a plurality of endothelial cell images photographed at a plurality of positions in a region adjacent to the central portion of the cornea simultaneously on the monitor.

3. The corneal endothelial cell photographing apparatus according to claim 1, further comprising
an operating unit,
wherein the display controller displays at least one of the plurality of endothelial cell images displayed on the monitor that is selected on the basis of an operation signal input from the operating unit in a magnified manner relative to the other endothelial cell images, and displays the analysis result for the magnified endothelial cell image.

4. The corneal endothelial cell photographing apparatus according to claim 1, wherein the display controller displays the plurality of endothelial cell images spaced apart from each other on the monitor.

5. The corneal endothelial cell photographing apparatus according to claim 1, further comprising
a photographing position changing unit for changing the photographing position for the plurality of endothelial cells on the cornea with respect to vertical and horizontal directions.

6. The corneal endothelial cell photographing apparatus according to claim 1, further comprising
a fixation optical system including a plurality of sight fixation lights for changing the line of sight of the examinee's eye.

7. The corneal endothelial cell photographing apparatus according to claim 1, further comprising
a drive unit for moving the illuminating optical system and the light receiving optical system in vertical and horizontal directions with respect to the examinee's eye.

8. The corneal endothelial cell photographing apparatus according to claim 1, wherein the display controller allocates a position display indicating the position of each of the plurality of endothelial cell images to each of the plurality of endothelial cell images.

9. The corneal endothelial cell photographing apparatus according to claim 1, wherein the display controller displays the analysis result for each of the plurality of endothelial cell images displayed on the monitor separately on the monitor.

10. The corneal endothelial cell photographing apparatus according to claim 1, wherein
the corneal endothelial cell photographing apparatus is a specular microscope, and
the illumination optical system and the light receiving optical system are symmetrically arranged with respect to a predetermined central axis so that the illumination optical system irradiates the cornea with the illuminating light in an oblique direction and the light receiving optical system receives the reflected light from the cornea in a specular direction of the cornea.

11. The corneal endothelial cell photographing apparatus according to claim 6, wherein the plurality of sight fixation lights comprise a center fixation lamp and a plurality of adjacent fixation lamps, the plurality of adjacent fixation lamps being arranged so that a visual axis of the examinee's eye to the adjacent fixation lamp is inclined with respect to a visual axis of the examinee's eye to the center fixation lamp at 4 to 6 degrees.

12. The corneal endothelial cell photographing apparatus according to claim 11, wherein the display controller displays simultaneously on the monitor the endothelial cell image photographed at the central portion of the cornea by using the center fixation lamp and a plurality of endothelial cell images photographed at a plurality of positions in a region adjacent to the central portion of the cornea by using the plurality of adjacent fixation lamps.

13. The corneal endothelial cell photographing apparatus according to claim 1, further comprising:
a fixation optical system comprising a plurality of sight fixation lights for changing a line of sight of the examinee's eye;
a memory comprising data of illumination positions of the plurality of sight fixation lights and an illumination order of the plurality of sight fixation lights; and
a controller for controlling the fixation optical system to light the sight fixation lights based on the data of the illumination positions and the illumination order of the plurality of sight fixation lights in the memory.

14. The corneal endothelial cell photographing apparatus according to claim 1, wherein the image processor comprises data of the integrated analysis result comprising the sum of numbers of endothelial cells analyzed in at least the two endothelial cell images photographed at different positions.

15. The corneal endothelial cell photographing apparatus according to claim 1, wherein the image processor comprises data of the integrated analysis result comprising the average value of endothelial cell densities analyzed in at least the two endothelial cell images photographed at different positions.

16. The corneal endothelial cell photographing apparatus according to claim 1, wherein the image processor comprises data of the integrated analysis result comprising the average value of coefficients of variation analyzed in at least the two endothelial cell images photographed at different positions.

17. The corneal endothelial cell photographing apparatus according to claim 1, wherein the image processor comprises data of the integrated analysis result comprising the average value of hexagonal cell appearance ratios analyzed in at least the two endothelial cell images photographed at different positions.

18. The corneal endothelial cell photographing apparatus according to claim 1, wherein the image processor comprises data of the integrated analysis result comprising the largest area of endothelial cells analyzed in at least the two endothelial cell images photographed at different positions.

* * * * *